(12) United States Patent
Xu et al.

(10) Patent No.: US 10,157,457 B2
(45) Date of Patent: *Dec. 18, 2018

(54) OPTICAL MEASUREMENT OF OPENING DIMENSIONS IN A WAFER

(71) Applicant: Zeta Instruments, Inc., San Jose, CA (US)

(72) Inventors: James Jianguo Xu, San Jose, CA (US); Ronny Soetarman, Fremont, CA (US); Ken Kinsun Lee, Los Altos Hills, CA (US); Nitigya Kathuria, San Jose, CA (US)

(73) Assignee: KLA-TENCOR CORPORATION, Milpitas, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 15/338,838

(22) Filed: Oct. 31, 2016

(65) Prior Publication Data

US 2018/0047148 A1 Feb. 15, 2018

Related U.S. Application Data

(63) Continuation-in-part of application No. 15/233,812, filed on Aug. 10, 2016.

(51) Int. Cl.
*G01N 21/88* (2006.01)
*G06T 7/00* (2017.01)
(Continued)

(52) U.S. Cl.
CPC ....... *G06T 7/0004* (2013.01); *G01N 21/8851* (2013.01); *G01N 21/9505* (2013.01);
(Continued)

(58) Field of Classification Search
CPC ........ G02B 21/06; G02B 21/00; G01N 21/64; G06K 9/00; H01L 21/67; H01L 21/66; H04N 13/02; H01J 37/28
See application file for complete search history.

(56) References Cited

U.S. PATENT DOCUMENTS 7,130,115 B2 * 10/2006 Olszak ................ G02B 21/002
                                                            359/372
7,729,049 B2 *  6/2010 Xu ........................ G02B 21/06
                                                            345/419
(Continued)

FOREIGN PATENT DOCUMENTS

JP          2015082095         4/2015

OTHER PUBLICATIONS

International Search Report and Written Opinion of International Search Authority for PCT/US2017/046076 dated Nov. 22, 2017 (7 pages).

*Primary Examiner* — Sathyanaraya V Perungavoor
*Assistant Examiner* — Philip P. Dang
(74) *Attorney, Agent, or Firm* — Imperium Patent Works LLP; Mark D. Marrello

(57) ABSTRACT

A method of generating 3D information of a sample using an optical microscope includes: varying the distance between the sample and an objective lens of the optical microscope at pre-determined steps, capturing an image at each pre-determined step, determining a characteristic value of each pixel in each captured image, determining a first captured image that is focused on a first surface of the sample based on the characteristic value of each pixel in each captured image, and determining a measurement of an opening in the first surface of the sample based on the first captured image. The first surface of the sample and the second surface of the sample are within a field of view of each of the captured images. The first captured image includes a pattern overlay. In another example, the opening measurement is determined using a second captured image without a pattern overlay.

19 Claims, 26 Drawing Sheets

SEMI-AUTOMATED 3-D METROLOGY SYSTEM

(51) Int. Cl.
   *G01N 21/95* (2006.01)
   *G02B 21/24* (2006.01)
   *G02B 21/36* (2006.01)

(52) U.S. Cl.
   CPC ......... *G02B 21/244* (2013.01); *G02B 21/367* (2013.01); *G01N 2021/8887* (2013.01); *G06T 2207/10056* (2013.01); *G06T 2207/30148* (2013.01)

(56) References Cited

U.S. PATENT DOCUMENTS

| | | | | |
|---|---|---|---|---|
| 9,460,557 | B1* | 10/2016 | Tran | B29C 64/386 |
| 2005/0285034 | A1* | 12/2005 | Tanaka | H01J 37/28 |
| | | | | 250/310 |
| 2006/0034543 | A1* | 2/2006 | Bacus | G02B 21/367 |
| | | | | 382/284 |
| 2006/0098861 | A1* | 5/2006 | See | G01B 11/08 |
| | | | | 382/145 |
| 2010/0135573 | A1* | 6/2010 | Xu | G02B 21/06 |
| | | | | 382/154 |
| 2012/0019626 | A1* | 1/2012 | Hou | G01N 21/956 |
| | | | | 348/50 |
| 2012/0176475 | A1* | 7/2012 | Xu | G02B 21/0092 |
| | | | | 348/46 |
| 2012/0223217 | A1* | 9/2012 | Zheng | B01L 3/508 |
| | | | | 250/215 |
| 2013/0280752 | A1* | 10/2013 | Ozcan | G01N 21/4795 |
| | | | | 435/29 |
| 2014/0163664 | A1* | 6/2014 | Goldsmith | A61B 17/00491 |
| | | | | 623/1.11 |
| 2015/0267892 | A1* | 9/2015 | Ikawa | H01L 33/58 |
| | | | | 362/84 |
| 2016/0261793 | A1* | 9/2016 | Sivan | H04N 19/597 |

* cited by examiner

SEMI-AUTOMATED 3-D METROLOGY SYSTEM

3-D IMAGING MICROSCOPE

METROLOGY SYSTEM

MULTIPLE IMAGES CAPTURED AT DIFFERENT DISTANCES

MAXIMUM CHARACTERISTIC VALUES FOR EACH PIXEL
LOCATION ACROSS ALL CAPTURED IMAGES

3-D IMAGE RESULTING FROM SELECTING MAXIMUM VALUES FOR
EACH X-Y PIXEL LOCATION ACROSS ALL Z-DIRECTION DISTANCES

SUMMATION MODE OPERATION
(SUM ALL CHARACTERISTIC VALUES FOR EACH CAPTURED IMAGE)

ERRONEOUS SURFACE DETECTION
DUE TO TRANSPARENT MATERIALS

RANGE MODE OPERATION
(COUNT ALL PIXELS WITH A CHARACTERISTIC VALUE
WITHIN A RANGE)

COUNT OF ALL PIXELS WITH CHARACTERISTIC VALUES
WITHIN A SECOND RANGE

PEAK MODE FLOWCHART

CAPTURED IMAGE

FIRST METHOD OF GENERATING INTENSITY THRESHOLD

SECOND METHOD OF GENERATING INTENSITY THRESHOLD

THIRD METHOD OF GENERATING INTENSITY THRESHOLD

3-D VIEW OF PR OPENING

2-D VIEW OF PR OPENING TOP SURFACE

2-D VIEW OF PR OPENING BOTTOM SURFACE

CAPTURED IMAGE FOCUSED ON TOP SURFACE OF PR LAYER

CAPTURED IMAGE FOCUSED ON BOTTOM SURFACE OF PR LAYER

CAPTURED IMAGE FOCUSED TOP SURFACE OF PHOTORESIST TRENCH

OPTICAL MEASUREMENT OF OPENING DIMENSIONS IN A WAFER

CROSS REFERENCE TO RELATED APPLICATIONS

This application is a continuation-in-part of, and claims priority under 35 U.S.C. § 120 from, nonprovisional U.S. patent application Ser. No. 15/233,812 entitled "AUTOMATED 3-D MEASUREMENT," filed on Aug. 10, 2016. The disclosure of which is incorporated herein by reference in its entirety.

TECHNICAL FIELD

The described embodiments relate generally to measuring 3-D information of a sample and more particularly to automatically measuring 3-D information in a fast and reliable fashion.

BACKGROUND INFORMATION

Three-dimensional (3-D) measurement of various objects or samples is useful in many different applications. One such application is during wafer level package processing. 3-D measurement information of a wafer during different steps of wafer level fabrication can provide insight as to the presence of wafer processing defects that may be present on the wafer. 3-D measurement information of the wafer during wafer level fabrication can provide insight as to the absence of defects before additional capital is expended to continue processing the wafer. 3-D measurement information of a sample is currently gathered by human manipulation of a microscope. The human user focuses the microscope using their eyes to determine when the microscope is focused on a surface of the sample. An improved method of gathering 3-D measurement information is needed.

SUMMARY

In a first novel aspect, three-dimensional (3-D) information of a sample using an optical microscope is generated by varying the distance between the sample and an objective lens of the optical microscope at pre-determined steps. An image is captured at each pre-determined step. The first surface of the sample and the second surface of the sample are within a field of view of each of the captured images. A characteristic value of each pixel in each captured image is determined. A first captured image that is focused on a first surface of the sample is determined based on the characteristic value of each pixel in each captured image. A measurement of an opening in the first surface of the sample is determined based on the first captured image.

In a second novel aspect, A three-dimensional (3-D) measurement system includes: an optical microscope comprising a objective lens and a stage, where the optical microscope is adapted to vary the distance between a sample supported by the stage and the objective lens of the optical microscope at pre-determined steps, and a computer system including: a processor and a storage device, where the computer system is adapted to: (i) store an image captured at each pre-determined step, where a first surface of the sample and a second surface of the sample are captured in each image, (ii) determine a characteristic of each pixel in each captured image, (iii) determining a first captured image that is focused on the first surface of the sample based on the characteristics of each pixel in each captured image, and (iv) determine a measurement of an opening in the first surface of the sample based on the first captured image.

In a third novel aspect, three-dimensional (3-D) information of a sample using an optical microscope is generated by (i) varying the distance between the sample and an objective lens of the optical microscope at pre-determined steps, (ii) capturing an image at each pre-determined step, where a pattern is projected onto the sample while each image is captured, and where a first surface of the sample and a second surface of the sample is within a field of view of each of the captured images, (iii) determining a characteristic value of each pixel in each captured image, (iv) determining a first captured image that is focused on a first surface of the sample based on the characteristic value of each pixel in each captured image, where the first captured image is focused at a focal distance, (v) capturing a second image taken at the focal distance, where a pattern is not projected onto the sample while the second image is captured, and (vi) determining a measurement of an opening in the first surface of the sample based on the second captured image.

Further details and embodiments and techniques are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to background examples and some embodiments of the invention, examples of which are illustrated in the accompanying drawings. In the description and claims below, relational terms such as "top", "down", "upper", "lower", "top", "bottom", "left" and "right" may be used to describe relative orientations between different parts of a structure being described, and it is to be understood that the overall structure being described can actually be oriented in any way in three-dimensional space.

Figure 1:
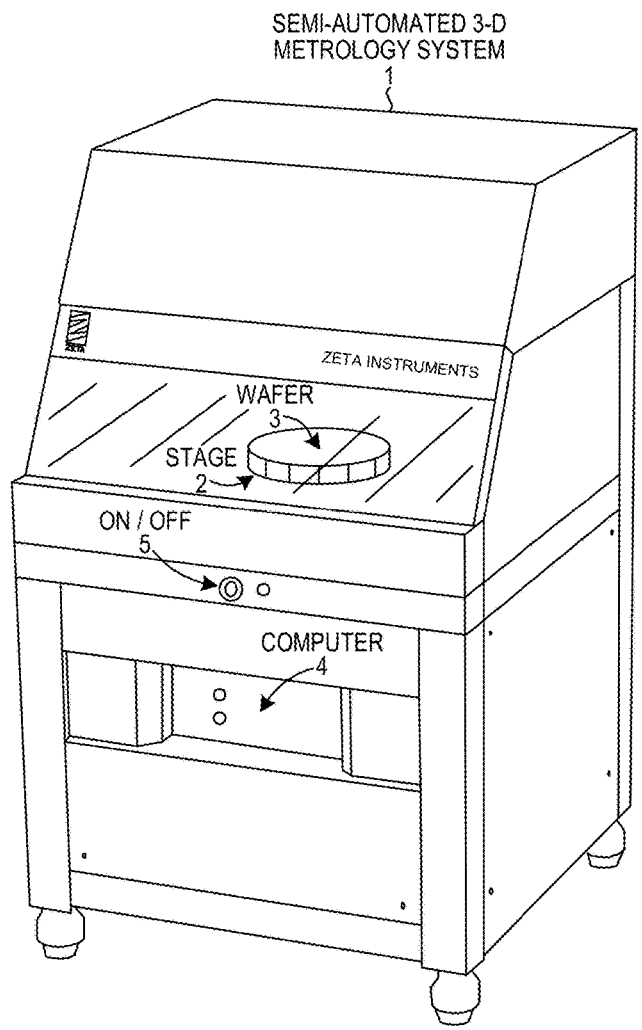
FIG. 1 is a diagram of a semi-automated 3-D metrology system 1 that performs automated 3-D measurement of a sample.

FIG. 1 is a diagram of a semi-automated 3-D metrology system 1. Semi-automated 3-D metrology system 1 includes an optical microscope (not shown), an ON/OFF button 5, a computer 4 and a stage 2. In operation, a wafer 3 is placed on the stage 2. The function of the semi-automated 3-D metrology system 1 is to capture multiple images of an object and generate 3-D information describing various surfaces of the object automatically. This is also referred to as a "scan" of an object. Wafer 3 is an example of an object that is analyzed by the semi-automated 3-D metrology system 1. An object may also be referred to as a sample. In operation, the wafer 3 is placed on stage 2 and the semi-automated 3-D metrology system 1 begins the process of automatically generating 3-D information describing the surfaces of the wafer 3. In one example, the semi-automated 3-D metrology system 1 is started by pressing a designated key on a keyboard (not shown) that is connected to computer 4. In another example, the automated 3-D metrology system 1 is started by sending a start command to the computer 4 across a network (not shown). Semi-automated 3-D metrology system 1 may also be configured to mate with an automated wafer handling system (not shown) that automatically removes a wafer once a scan of the wafer is completed and inserts a new wafer for scanning.

A fully automated 3-D metrology system (not shown) is similar to the semi-automated 3-D metrology system of FIG. 1; however, a fully automated 3-D metrology system also includes a robotic handler that can automatically pick up a wafer and place the wafer onto the stage without human intervention. In a similar fashion, a fully automated 3-D metrology system can also use the robotic handler to automatically pickup a wafer from the stage and remove the wafer from the stage. A fully automated 3-D metrology system is desirable during the production of many wafers because it avoids possible contamination by a human operator and improves time efficiency and overall cost. Alternatively, the semi-automated 3-D metrology system 1 is desirable during research and development activities when only a small number of wafers need to be measured.

Figure 2:
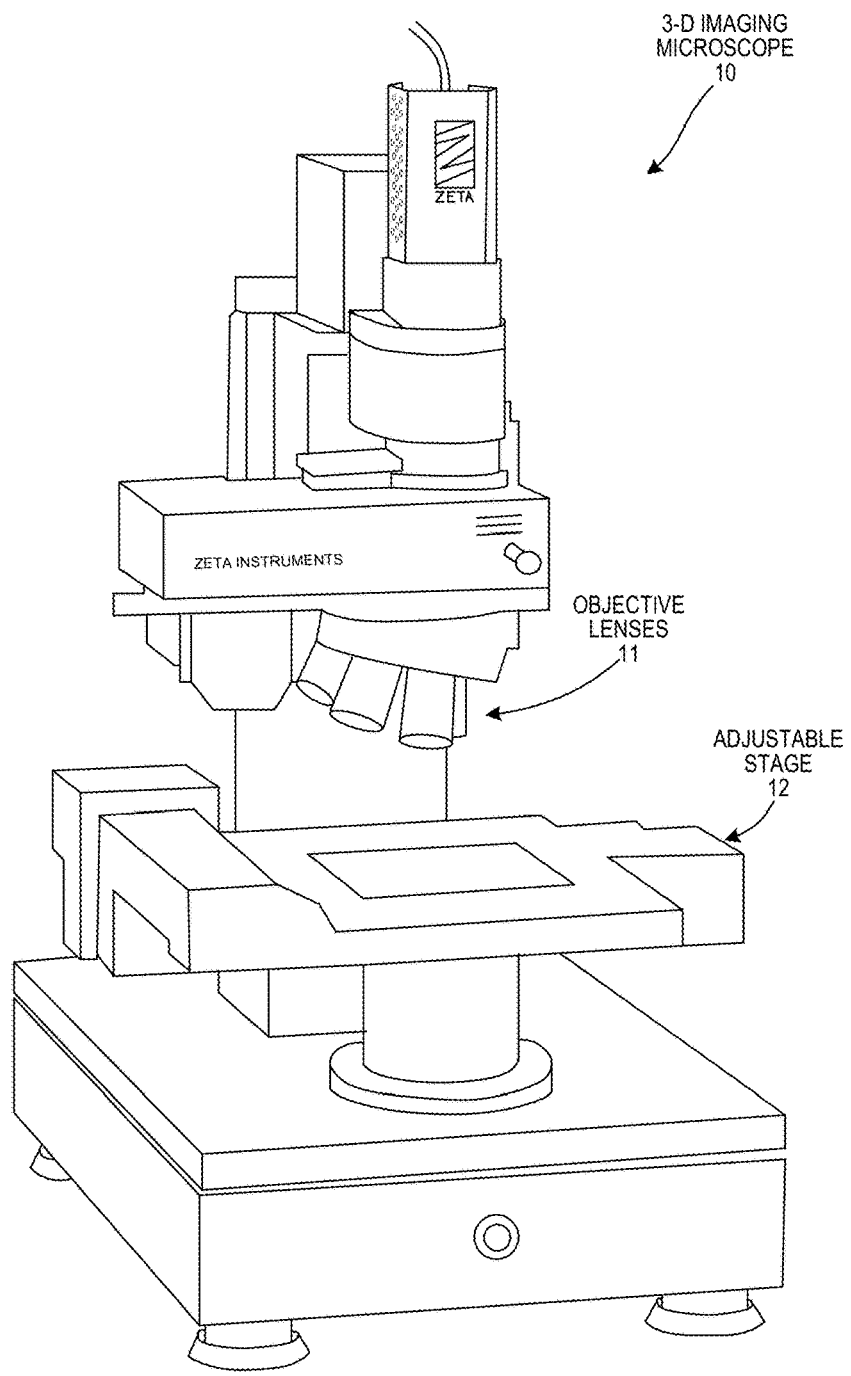
FIG. 2 is a diagram of a 3-D imaging microscope 10 including adjustable objective lenses 11 and an adjustable stage 12.

FIG. 2 is a diagram of a 3-D imaging microscope 10 including multiple objective lenses 11 and an adjustable stage 12. 3-D imaging microscope may be a confocal microscope, a structured illumination microscope, an interferometer microscope or any other type of microscope well known in the art. A confocal microscope will measure intensity. A structured illumination microscope will measure contrast of a projected structure. An interferometer microscope will measure interference fringe contrast.

In operation, a wafer is placed on adjustable stage 12 and an objective lens is selected. The 3-D imaging microscope 10 captures multiple images of the wafer as the height of the stage, on which the wafer rests, is adjusted. This results in multiple images of the wafer to be captured while the wafer is located at various distances away from the selected lens. In one alternate example, the wafer is placed on a fixed stage and the position of the objective lens is adjusted, thereby varying the distance between the objective lens and the sample without moving the stage. In another example, the stage is adjustable in the x-y direction and the objective lens is adjustable in the z-direction.

The captured images may be stored locally in a memory included in 3-D imaging microscope 10. Alternatively, the captured images may be stored in a data storage device included in a computer system, where the 3-D microscope 10 communicates the captured images to the computer system across a data communication link. Examples of a data communication link include: a Universal Serial Bus (USB) Interface, an ethernet connection, a FireWire bus interface, a wireless network such as WiFi.

Figure 3:
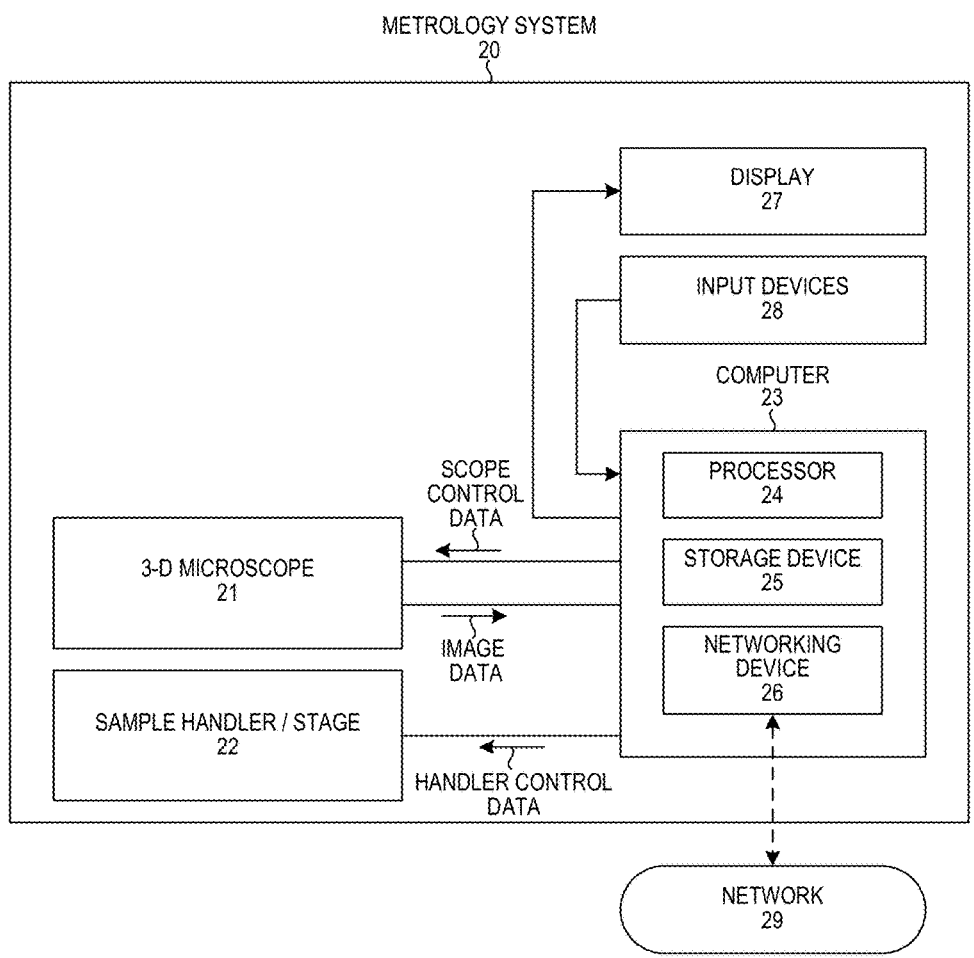
FIG. 3 is a diagram of a 3-D metrology system 20 including a 3-D microscope, a sample handler, a computer, a display, and input devices.

FIG. 3 is a diagram of a 3-D metrology system 20 including a 3-D microscope 21, a sample handler 22, a computer 23, a display 27 (optional), and input devices 28. 3-D metrology system 20 is an example of a system that is included in semi-automated 3-D metrology system 1. Computer 23 includes a processor 24, a storage device 25, and a network device 26 (optional). The computer outputs information to a user via display 27. The display 27 may be used as an input device as well if the display is a touch screen device. Input devices 28 may include a keyboard and a mouse. The computer 23 controls the operation of 3-D microscope 21 and sample handler/stage 22. When a start scan command is received by the computer 23, the computer sends one or more commands to configure the 3-D microscope for image capturing ("scope control data"). For example, the correct objective lens needs to be selected, the resolution of the images to be captured needs to be selected, and the mode of storing captured images needs to be selected. When a start scan command is received by the computer 23, the computer sends one or more commands to configure the sample handler/stage 22 ("handler control data"). For example, the correct height (z-direction) adjustment needs to be selected and the correct horizontal (x-y dimension) alignment needs to be selected.

During operation, the computer 23 causes sample handler/stage 22 to be adjusted to the proper position. Once the sample handler/stage 22 is properly positioned, the computer 23 will cause the 3-D microscope to focus on a focal plane and capture at least one image. The computer 23 will then cause that stage to be move in the z-direction such that the distance between the sample and the objective lens of the optical microscope is changed. Once the stage is moved to the new position, the computer 23 will cause the optical microscope to capture a second image. This process continues until an image is captured at each desired distance between the objective lens of the optical microscope and the sample. The images captured at each distance are communicated from 3-D microscope 21 to computer 23 ("image data"). The captured images are stored in storage device 25 included in computer 23. In one example, the computer 23 analyzes the captured images and outputs 3-D information to display 27. In another example, computer 23 analyzes the captured images and outputs 3-D information to a remote device via network 29. In yet another example, computer 23 does not analyze the captured images, but rather sends the captured images to another device via network 29 for processing. 3-D information may include a 3-D image rendered based on the captured images. 3-D information may not include any images, but rather include data based on various characteristics of each captured image.

Figure 4:
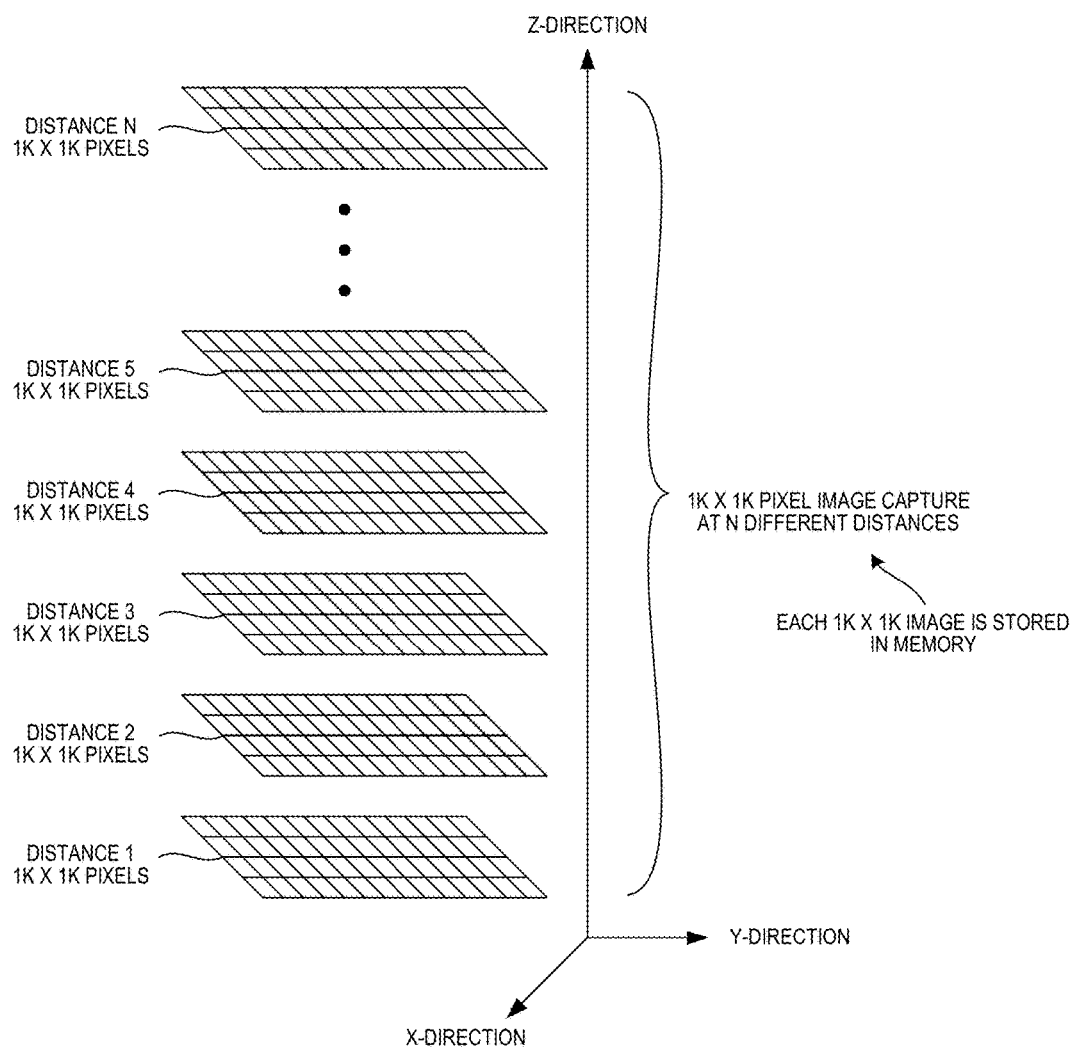
FIG. 4 is a diagram illustrating a method of capturing images as the distance between the objective lens of the optical microscope and the stage is varied.

FIG. 4 is a diagram illustrating a method of capturing images as the distance between the objective lens of the optical microscope and the sample is varied. In the embodiment illustrated in FIG. 4, each image includes one-thousand by one-thousand pixels. In other embodiments, the image may include various configurations of pixels. In one example, the spacing between consecutive distances is fixed to be a predetermined amount. In another example, the spacing between consecutive distances may not be fixed. This no fixed spacing between images in the z-direction may be advantageous in the event that additional z-direction resolution is required for only a portion of the z-direction scan of the sample. The z-direction resolution is based on the number of images captured per unit length in the z-direction, therefore capturing additional image images per unit length in the z-direction will increase the z-direction resolution measured. Conversely, capturing fewer images per unit length in the z-direction will decrease the z-direction resolution measured.

As discussed above, the optical microscope is first adjusted to be focused on a focal plane located at distance 1 away from an objective lens of the optical microscope. The optical microscope then captures an image that is stored in a storage device (i.e. "memory"). The stage is then adjusted to such that the distance between the objective lens of the optical microscope and the sample is distance 2. The optical microscope then captures an image that is stored in the storage device. The stage is then adjusted to such that the distance between the objective lens of the optical microscope and the sample is distance 3. The optical microscope then captures an image that is stored in the storage device. The stage is then adjusted to such that the distance between the objective lens of the optical microscope and the sample is distance 4. The optical microscope then captures an image that is stored in the storage device. The stage is then adjusted to such that the distance between the objective lens of the optical microscope and the sample is distance 5. The optical microscope then captures an image that is stored in the storage device. The process is continued for N different distances between the objective lens of the optical microscope and the sample. Information indicating which image is associated with each distance is also stored in the storage device for processing.

In an alternative embodiment, the distance between the objective lens of the optical microscope and the sample is fixed. Rather, the optical microscope includes a zoom lens that allows the optical microscope to vary the focal plane of the optical microscope. In this fashion, the focal plane of the optical microscope is varied across N different focal planes while the stage, and the sample supported by the stage, is stationary. An image is captured for each focal plane and stored in a storage device. The captured images across all the various focal planes are then processed to determine 3-D information of the sample. This embodiment requires a zoom lens that can provide sufficient resolution across all focal planes and that introduces minimal image distortion. Additionally, calibration between each zoom position and resulting focal length of the zoom lens is required.

Figure 5:
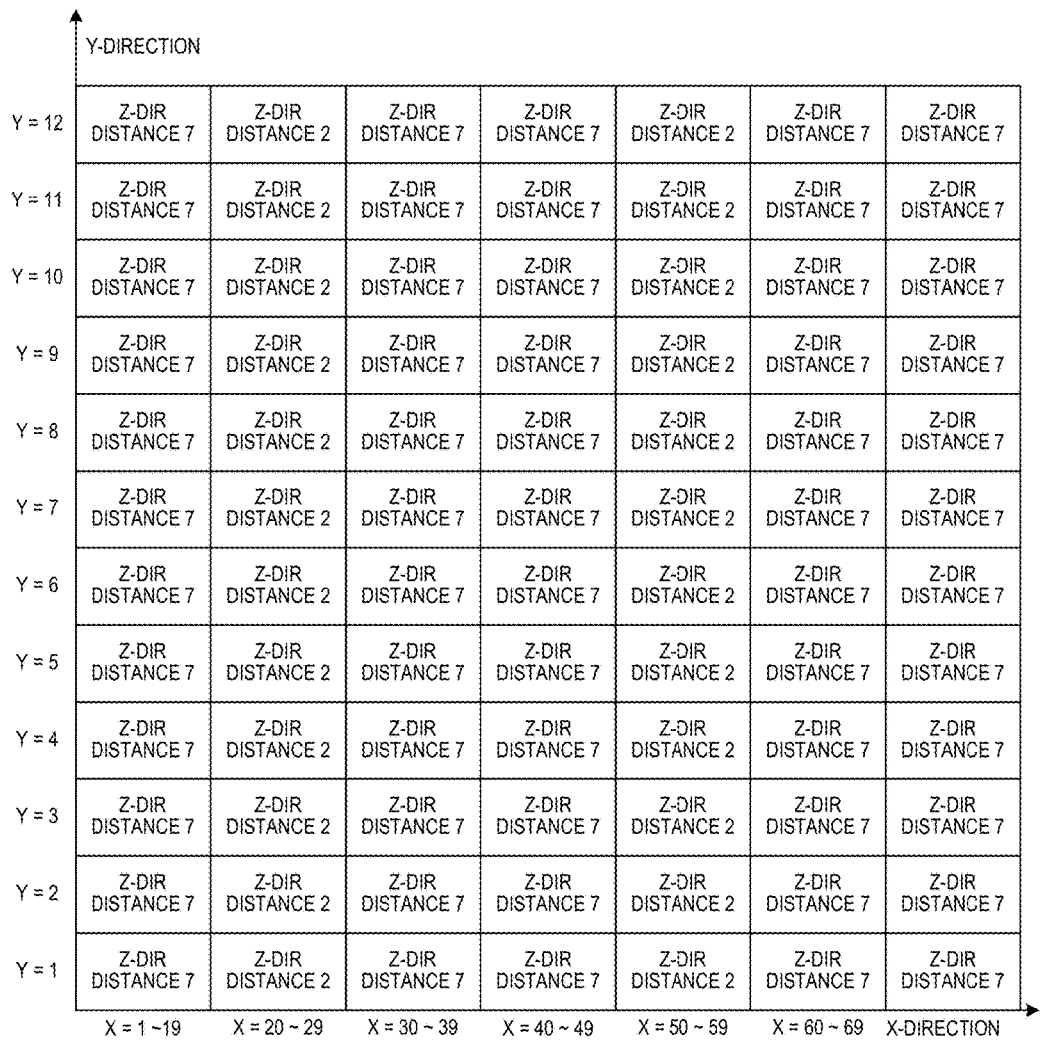
FIG. 5 is a chart illustrating the distance between the objective lens of the optical microscope and the sample surface for which each x-y coordinate had the maximum characteristic value.

FIG. 5 is a chart illustrating the distance between the objective lens of the optical microscope and the sample for which each x-y coordinate had the maximum characteristic value. Once images are captured and stored for each distance, characteristics of each pixel of each image can be analyzed. For example, the intensity of the light of each pixel of each image can be analyzed. In another example, the contrast of each pixel of each image can be analyzed. In yet another example, the fringe contrast of each pixel of each image can be analyzed. The contrast of a pixel may be determined by comparing the intensity of a pixel with that of a preset number of surrounding pixels. For additional description regarding how to generate contrast information, see U.S. patent application Ser. No. 12/699,824, entitled "3-D Optical Microscope", filed Feb. 3, 2010, by James Jianguo Xu et al. (the subject matter of which is incorporated herein by reference).

Figure 6:
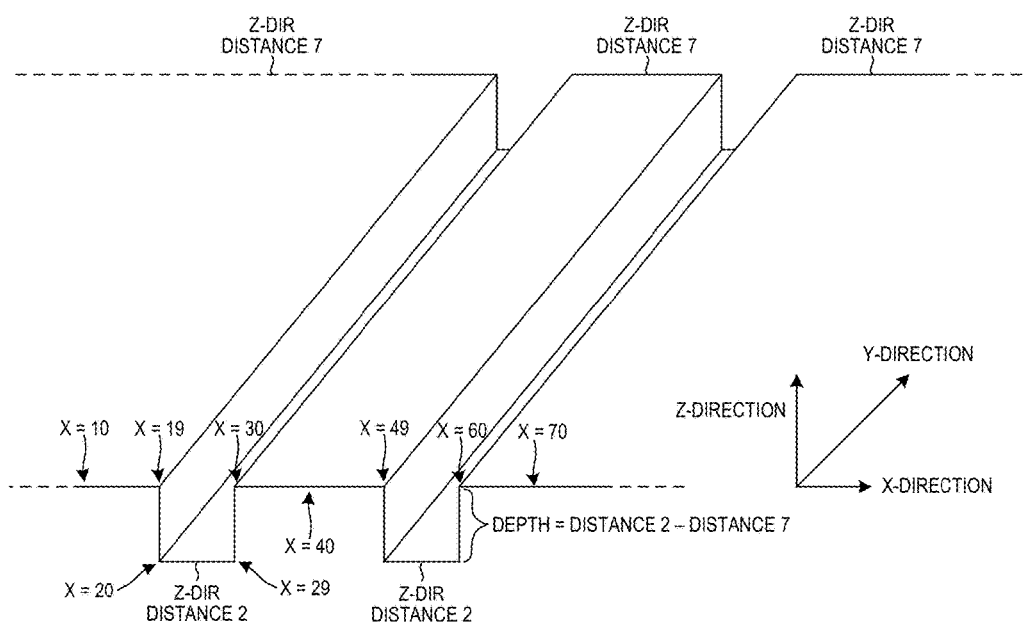
FIG. 6 is a 3-D diagram of an image rendered using the maximum characteristic value for each x-y coordinate shown in FIG. 5.

FIG. 6 is a 3-D diagram of a 3-D image rendered using the maximum characteristic value for each x-y coordinate shown in FIG. 5. All pixels with an X location between 1 and 19 have a maximum characteristic value at z-direction distance 7. All pixels with an X location between 20 and 29 have a maximum characteristic value at z-direction distance 2. All pixels with an X location between 30 and 49 have a maximum characteristic value at z-direction distance 7. All pixels with an X location between 50 and 59 have a maximum characteristic value at z-direction distance 2. All pixels with an X location between 60 and 79 have a maximum characteristic value at z-direction distance 7. In this fashion, the 3-D image illustrated in FIG. 6 can be created using the maximum characteristic value per x-y pixel across all captured images. Additionally, given that distance 2 is known and that distance 7 is known, the depth of the well illustrated in FIG. 6 can be calculated by subtracting distance 7 from distance 2.

Peak Mode Operation

Figure 7:
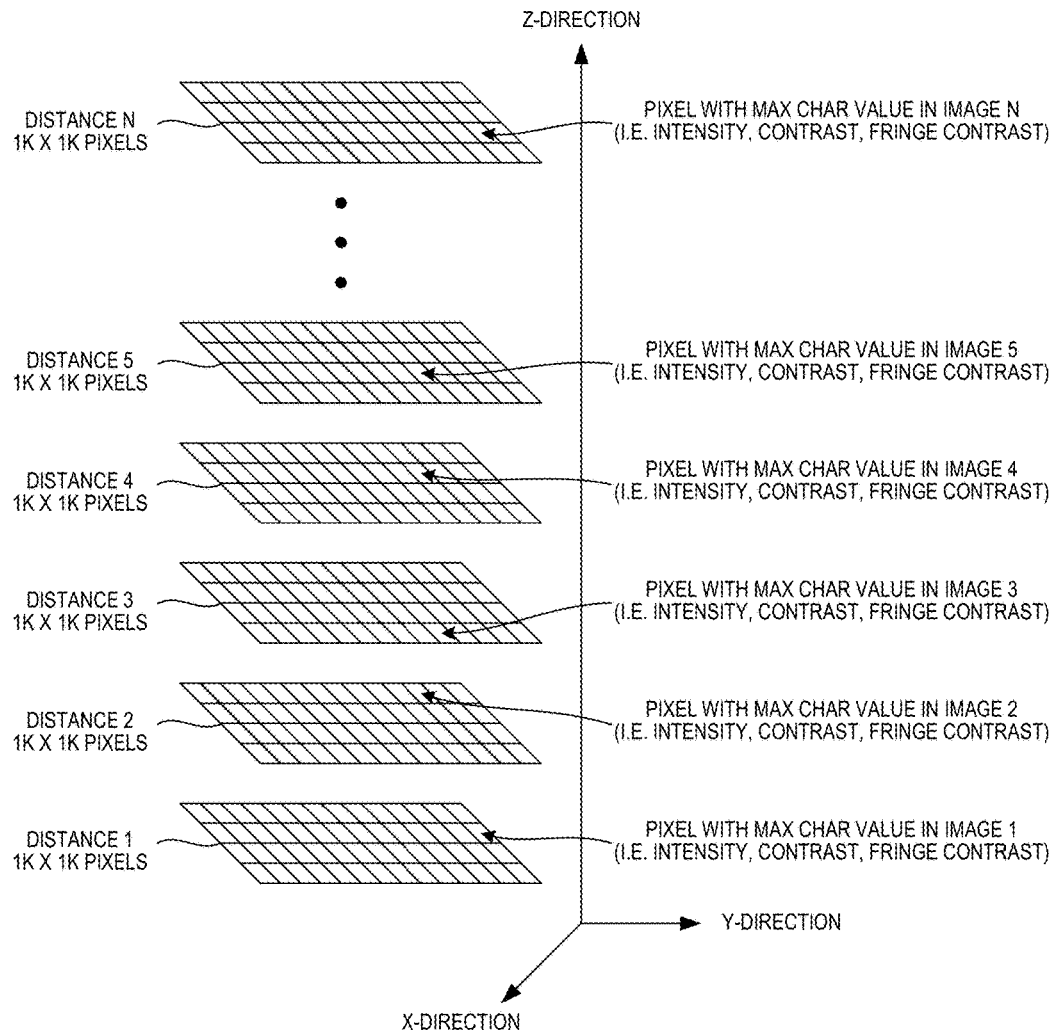
FIG. 7 is a diagram illustrating peak mode operation using images captured at various distances.

FIG. 7 is a diagram illustrating peak mode operation using images captured at various distances. As discussed regarding FIG. 4 above, the optical microscope is first adjusted to be focused on a plane located at distance 1 away from an objective lens of the optical microscope. The optical microscope then captures an image that is stored in a storage device (i.e. "memory"). The stage is then adjusted to such that the distance between the objective lens of the optical microscope and the sample is distance 2. The optical microscope then captures an image that is stored in the storage device. The stage is then adjusted to such that the distance between the objective lens of the optical microscope and the sample is distance 3. The optical microscope then captures an image that is stored in the storage device. The stage is then adjusted to such that the distance between the objective lens of the optical microscope and the sample is distance 4. The optical microscope then captures an image that is stored in the storage device. The stage is then adjusted to such that the distance between the objective lens of the optical microscope and the sample is distance 5. The optical microscope then captures an image that is stored in the storage device. The process is continued for N different distances between the objective lens of the optical microscope and the stage. Information indicating which image is associated with each distance is also stored in the storage device for processing.

Instead of determining the maximum characteristic value for each x-y location across all captured images at various z-distances, the maximum characteristic value across all x-y locations in a single captured image at one z-distance is determined in peak mode operation. Said another way, for each captured image the maximum characteristic value across all pixels included in the captured image is selected. As illustrated in FIG. 7, the pixel location with the maximum characteristic value will likely vary between different captured images. The characteristic may be intensity, contrast, or fringe contrast.

Figure 8:
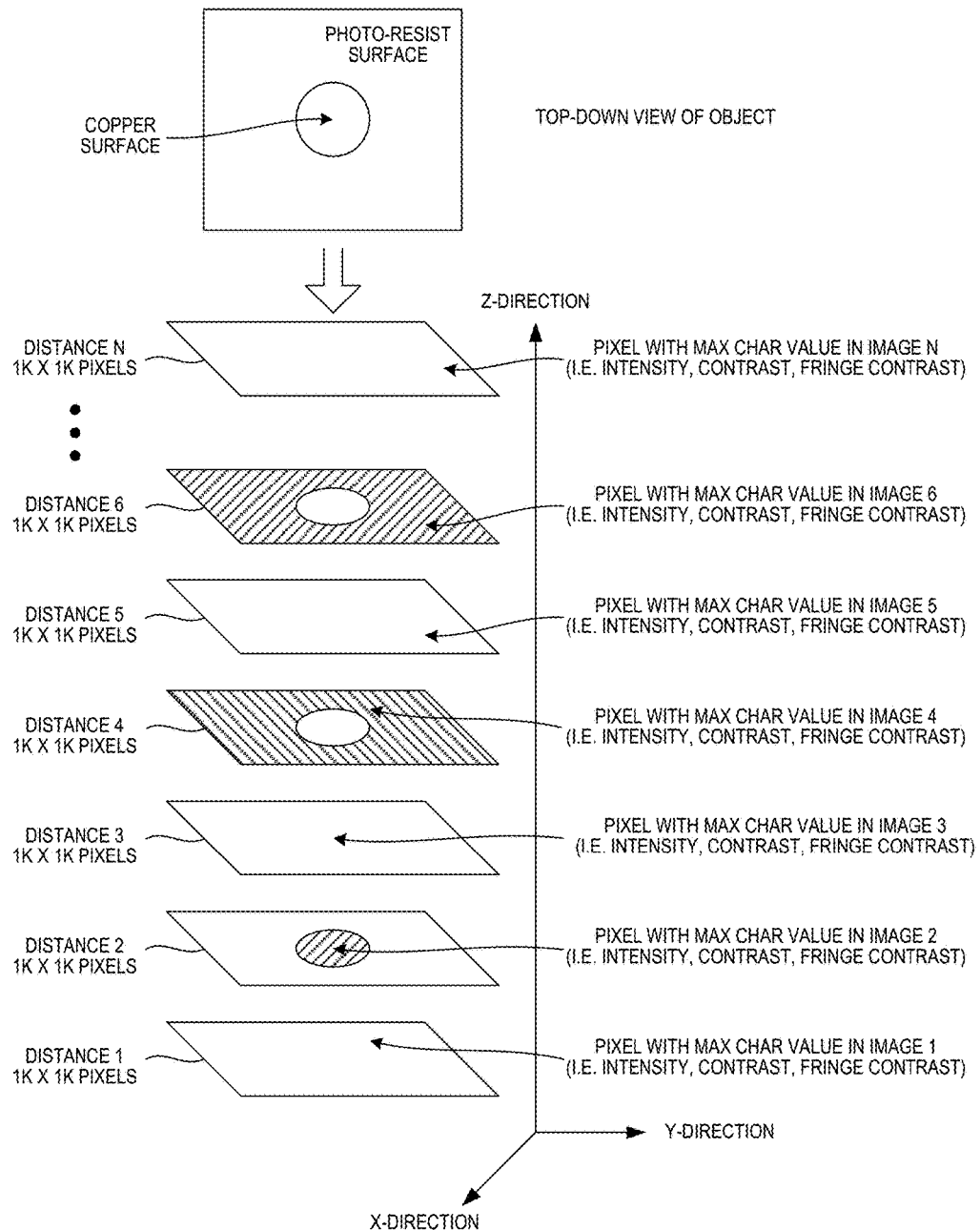
FIG. 8 is a diagram illustrating peak mode operation using images captured at various distances when a photoresist opening is within the field of view of the optical microscope.
Figure 11:
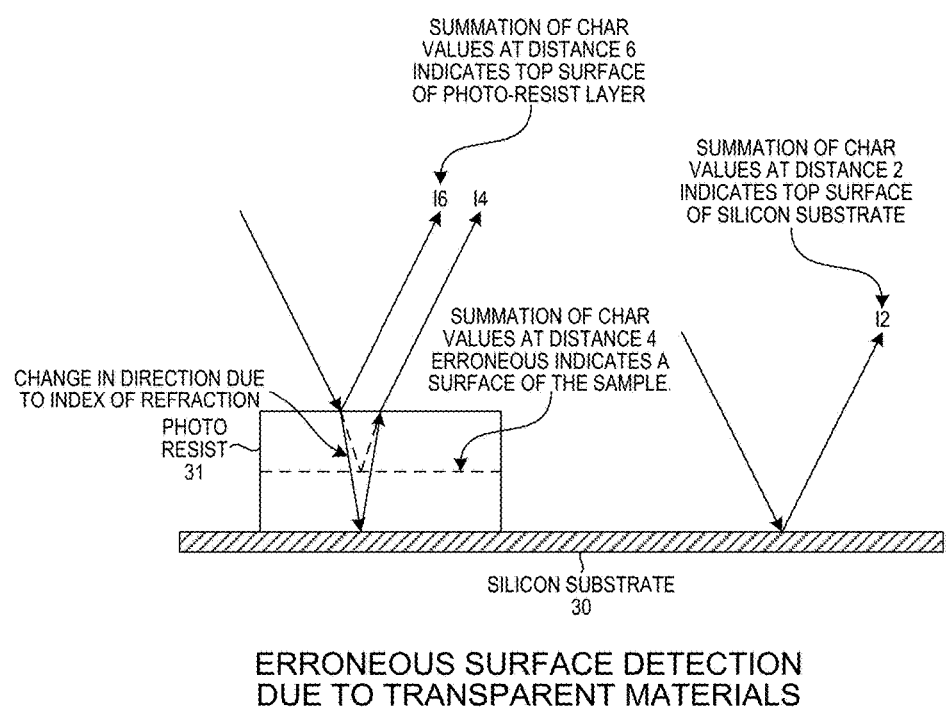
FIG. 11 is a diagram illustrating erroneous surface detection when using summation mode operation.

FIG. 8 is a diagram illustrating peak mode operation using images captured at various distances when a photoresist (PR) opening is within the field of view of the optical microscope. The top-down view of the object shows the cross-section area of the PR opening in the x-y plane. The PR opening also has a depth of specific depth in the z-direction. The images captured at various distances are shown below the top-down view in FIG. 8. At distance 1, the optical microscope is not focused on the top surface of the wafer or the bottom surface of the PR opening. At distance 2, the optical microscope is focused on the bottom surface of the PR opening, but is not focused on the top surface of the wafer. This results in an increased characteristic value (intensity/contrast/fringe contrast) in the pixels that receive light reflecting from the bottom surface of the PR opening compared to the pixels that receive reflected light from other surfaces that are out of focus (top surface of the wafer). At distance 3, the optical microscope is not focused on the top surface of the wafer or the bottom surface of the PR opening. Therefore, at distance 3 the maximum characteristic value will be substantially lower than the maximum characteristic value measured at distance 2. At distance 4, the optical microscope is not focused on any surface of the sample; however, due to the difference of the index of refraction of air and the index of refraction of the photoresist layer an increase in the maximum characteristic value (intensity/contrast/fringe contrast) is measured. FIG. 11 and the accompanying text describe this phenomenon in greater detail. At distance 6, the optical microscope is focused on the top surface of the wafer, but is not focused on the bottom surface of the PR opening. This results in an increased characteristic value (intensity/contrast/fringe contrast) in the pixels that receive light reflected from the top surface of the wafer compared to the pixels that receive reflected light from other surfaces that are out of focus (bottom surface of the PR opening). Once the maximum characteristic value from each captured image is determined, the results can be utilized to determine at which distances a surface of the wafer is located.

Figure 9:
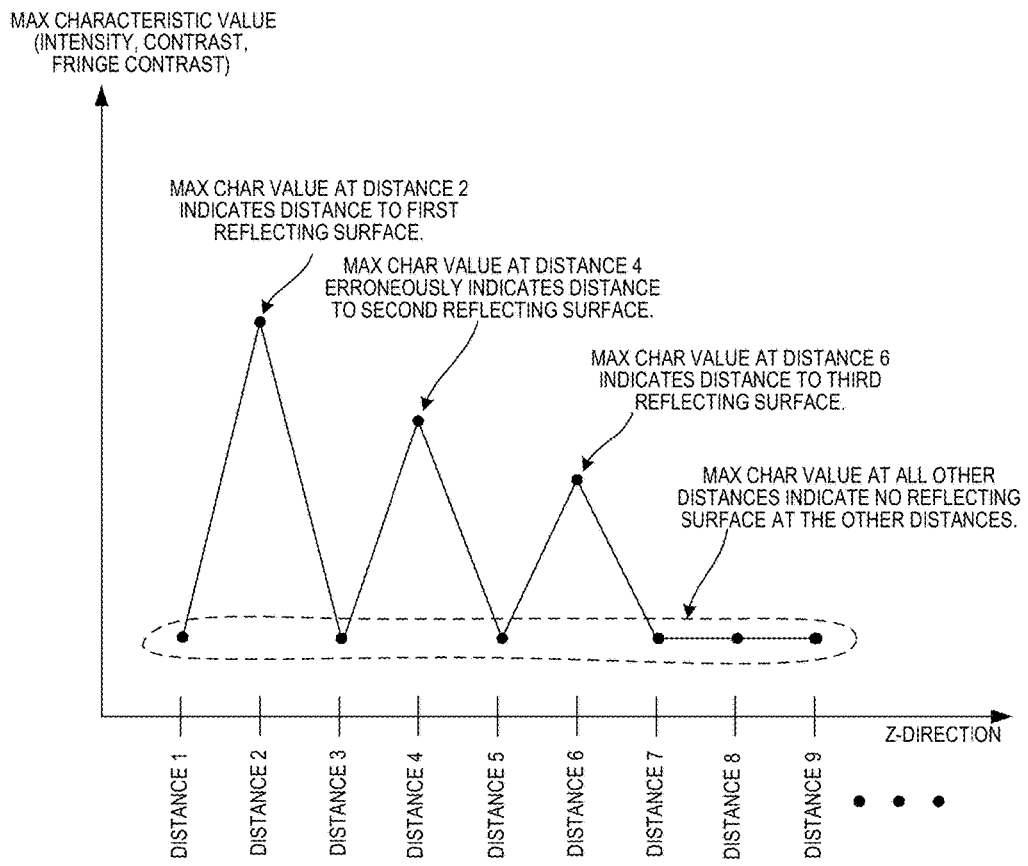
FIG. 9 is a chart illustrating the 3-D information resulting from the peak mode operation.

FIG. 9 is a chart illustrating the 3-D information resulting from the peak mode operation. As discussed regarding FIG. 8, the maximum characteristic value of the images captured at distances 1, 3 and 5 have a lower maximum characteristic value compared to the maximum characteristic value of the images captured at distances 2, 4 and 6. The curve of the maximum characteristics values at various z-distances may contain noise due to environmental effects, such as vibration. To minimize such noise, a standard smoothing method, such as Gaussian filtering with certain kernel size, can be applied before further data analysis.

One method of comparing the maximum characteristics values is performed by a peak finding algorithm. In one example, a derivative method is used to locate zero crossing point along the z-axis to determine the distance at which each "peak" is present. The maximum characteristic value at each distance where a peak is found is then compared to determine the distance where the greatest characteristic value was measured. In the case of FIG. 9, a peak will be found at distance 2, which is used as an indication that a surface of the wafer is located at distance 2.

Another method of comparing the maximum characteristics values is performed by comparing each maximum characteristic value with a preset threshold value. The threshold value may be calculated based on the wafer materials, distances, and the specification of the optical microscope. Alternatively, the threshold value may be determined by empirical testing before automated processing. In either case, the maximum characteristic value for each captured image is compared to the threshold value. If the maximum characteristic value is greater than the threshold, then it is determined that the maximum characteristic value indicates the presence of a surface of the wafer. If the maximum characteristic value is not greater than the threshold, then it is determined that the maximum characteristic value does not indicate a surface of the wafer.

Summation Mode Operation

Figure 10:
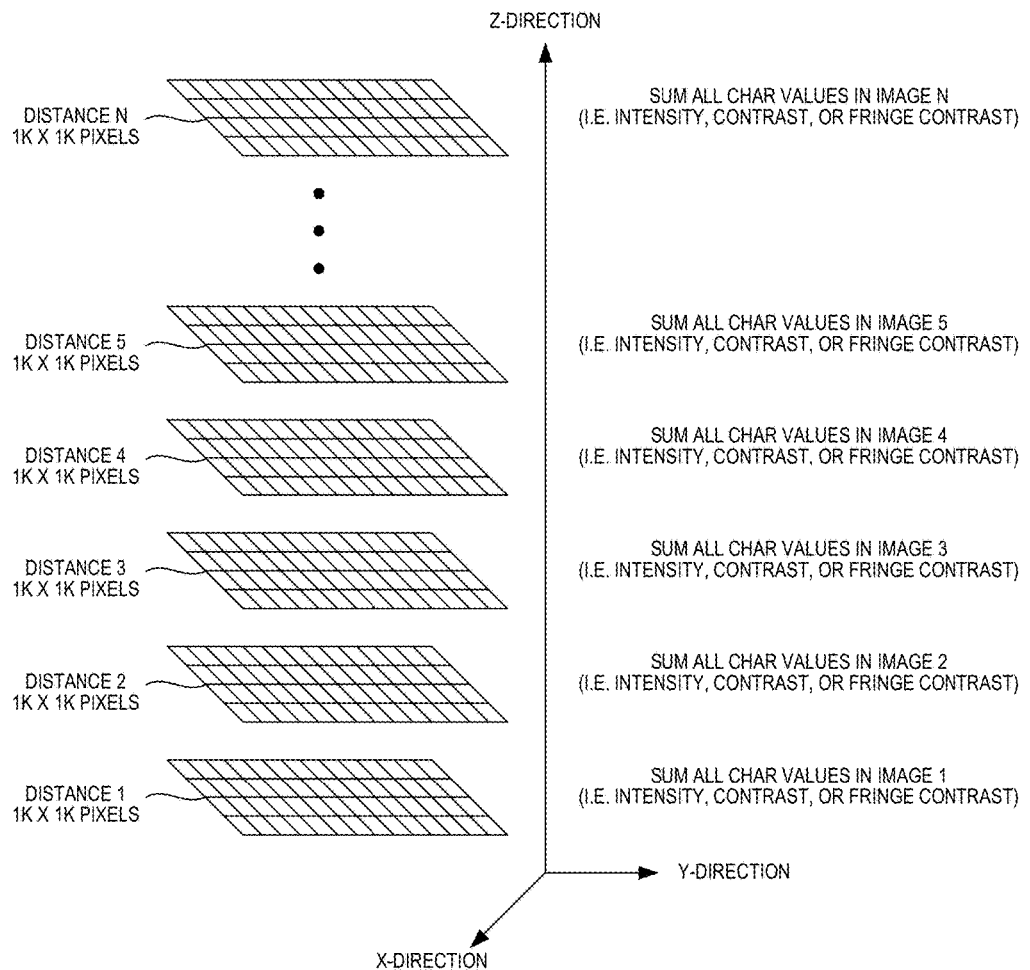
FIG. 10 is a diagram illustrating summation mode operation using images captured at various distances.

FIG. 10 is a diagram illustrating summation mode operation using images captured at various distances. As discussed regarding FIG. 4 above, the optical microscope is first adjusted to be focused on a plane located at distance 1 away from an objective lens of the optical microscope. The optical microscope then captures an image that is stored in a storage device (i.e. "memory"). The stage is then adjusted to such that the distance between the objective lens of the optical microscope and the sample is distance 2. The optical microscope then captures an image that is stored in the storage device. The stage is then adjusted such that the distance between the objective lens of the optical microscope and the sample is distance 3. The optical microscope then captures an image that is stored in the storage device. The stage is then adjusted to such that the distance between the objective lens of the optical microscope and the sample is distance 4. The optical microscope then captures an image that is stored in the storage device. The stage is then adjusted to such that the distance between the objective lens of the optical microscope and the sample is distance 5. The optical microscope then captures an image that is stored in the storage device. The process is continued for N different distances between the objective lens of the optical microscope and the sample. Information indicating which image is associated with each distance is also stored in the storage device for processing.

Instead of determining the maximum characteristic value across all x-y locations in a single captured image at one z-distance, the characteristic values of all x-y locations of each captured image are added together. Said another way, for each captured image the characteristic values for all pixels included in the captured image are summed together. The characteristic may be intensity, contrast, or fringe contrast. A summed characteristics value that is substantially greater than the average summed characteristic value of neighboring z-distances indicates that a surface of the wafer is present at the distance. However, this method can also result in false positives as described in FIG. 11.

FIG. 11 is a diagram illustrating erroneous surface detection when using summation mode operation. The wafer illustrated in FIG. 11 includes a silicon substrate 30 and a photoresist layer 31 deposited on top of the silicon substrate 30. The top surface of the silicon substrate 30 is located at distance 2. The top surface of the photoresist layer 31 is located at distance 6. The image captured at distance 2 will result in a summation of characteristic values that is substantially greater than other images captured at distances where a surface of the wafer is not present. The image captured at distance 6 will result in a summation of characteristic values that is substantially greater than other images captured at distances where a surface of the wafer is not present. At this point, the summation mode operation seems to be a valid indicator of the presence of a surface of the wafer. However, the image captured at distance 4 will result in a summation of characteristic values that is substantially greater than other images captured at distances where a surface of the wafer is not present. This is a problem because, as is clearly shown in FIG. 11, a surface of the wafer is not located at distance 4. Rather, the increase in the summation of characteristics values at distance 4 is an artifact of the surfaces located at distances 2 and 6. A major portion of the light that irradiates the photoresist layer does not reflect, but rather travels into the photoresist layer. The angle at which this light travels is changed due to the difference of the index of refraction of air and photoresist. The new angle is closer to normal than the angle of the light irradiating the top surface of the photoresist. The light travels to the top surface of the silicon substrate beneath the photoresist layer. The light is then reflected by the highly reflected silicon substrate layer. The angle of the reflected light is changed again as the reflected light leaves the photoresist layer and enters the air due to the difference in the index of refraction between air and the photoresist layer. This first redirecting, reflecting, and second redirecting of the irradiating light causes the optical microscope to observe an increase in characteristic values (intensity/contrast/fringe contrast) at distance 4. This example illustrates that whenever a sample includes a transparent material, the summation mode operation will detect surfaces that are not present on the sample.

Figure 12:
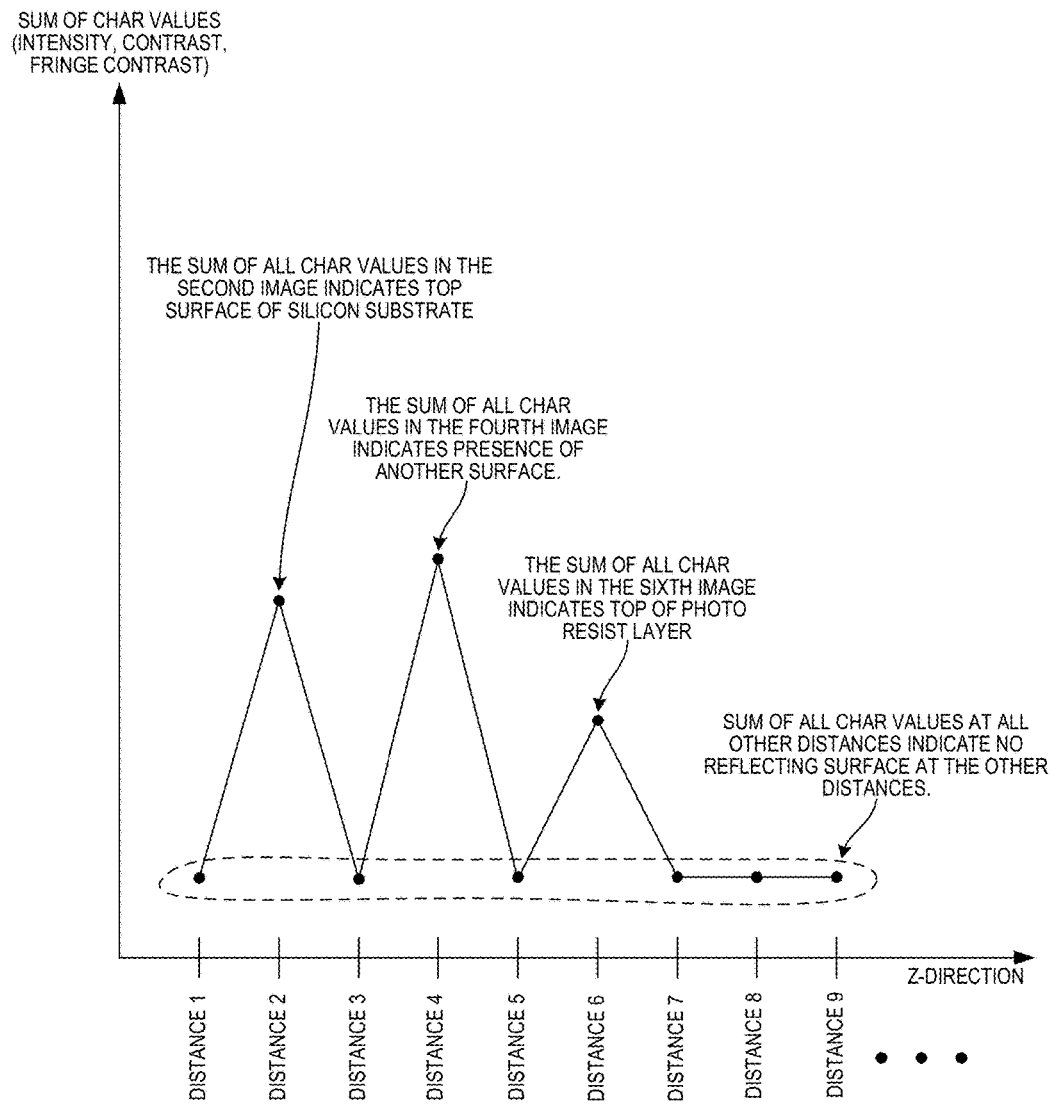
FIG. 12 is a chart illustrating the 3-D information resulting from the summation mode operation.

FIG. 12 is a chart illustrating the 3-D information resulting from the summation mode operation. This chart illustrates the result of the phenomenon illustrated in FIG. 11. The large value of summed characteristic values at distance 4 erroneously indicates the present of a surface at distance 4. A method that does not result in false positive indications of the presence of surface of the wafer is needed.

Range Mode Operation

Figure 13:
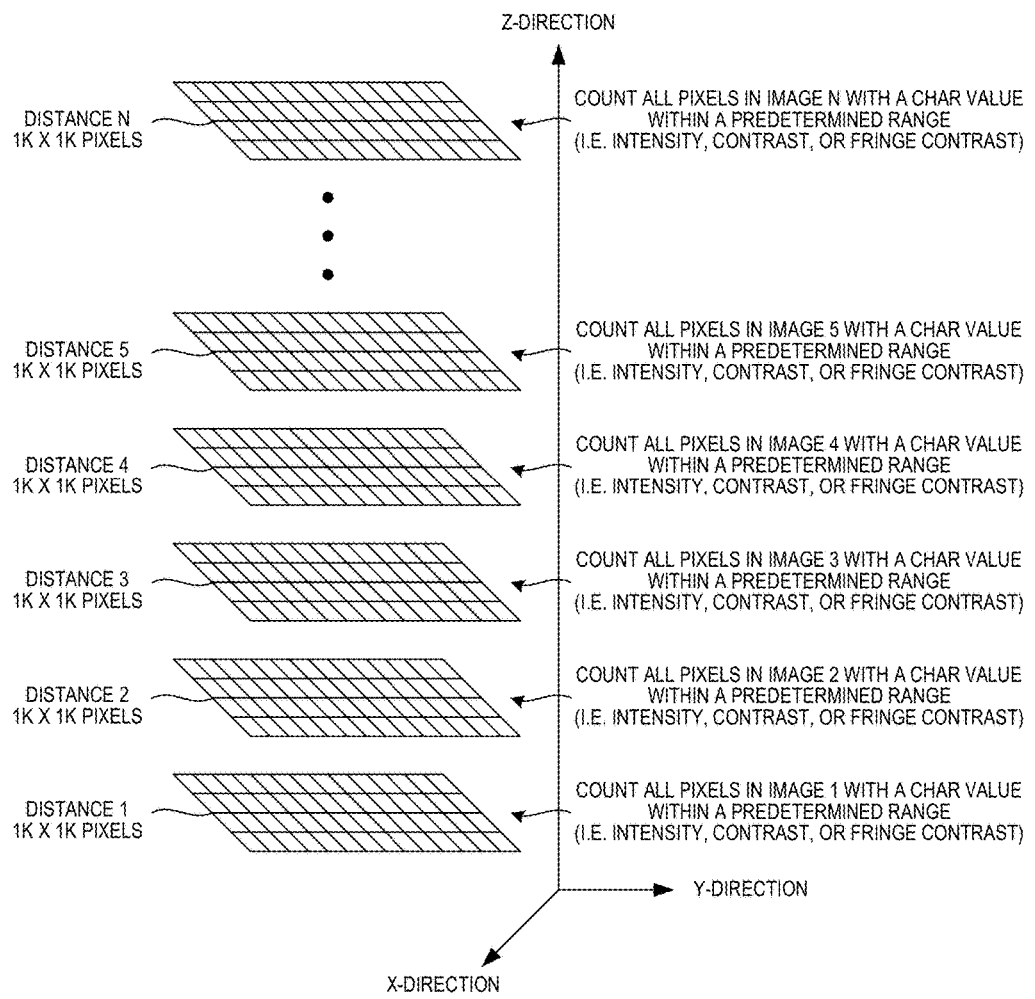
FIG. 13 is a diagram illustrating range mode operation using images captured at various distances.

FIG. 13 is a diagram illustrating range mode operation using images captured at various distances. As discussed regarding FIG. 4 above, the optical microscope is first adjusted to be focused on a plane located at distance 1 away from an objective lens of the optical microscope. The optical microscope then captures an image that is stored in a storage device (i.e. "memory"). The stage is then adjusted to such that the distance between the objective lens of the optical microscope and the sample is distance 2. The optical microscope then captures an image that is stored in the storage device. The stage is then adjusted to such that the distance between the objective lens of the optical microscope and the sample is distance 3. The optical microscope then captures an image that is stored in the storage device. The stage is then adjusted to such that the distance between the objective lens of the optical microscope and the sample is distance 4. The optical microscope then captures an image that is stored in the storage device. The stage is then adjusted such that the distance between the objective lens of the optical microscope and the sample is distance 5. The optical microscope then captures an image that is stored in the storage device. The process is continued for N different distances between the objective lens of the optical microscope and the sample. Information indicating which image is associated with each distance is also stored in the storage device for processing.

Instead of determining the summation of all characteristic values across all x-y locations in a single captured image at one z-distance, a count of pixels that have a characteristic value within a specific range that are included in the single captured image is determined. Said another way, for each captured image a count of pixels that have a characteristic value within a specific range is determined. The characteristic may be intensity, contrast, or fringe contrast. A count of pixels at one particular z-distance that is substantially greater than the average count of pixels at neighboring z-distances indicates that a surface of the wafer is present at the distance. This method reduces the false positives described in FIG. 11.

Figure 14:
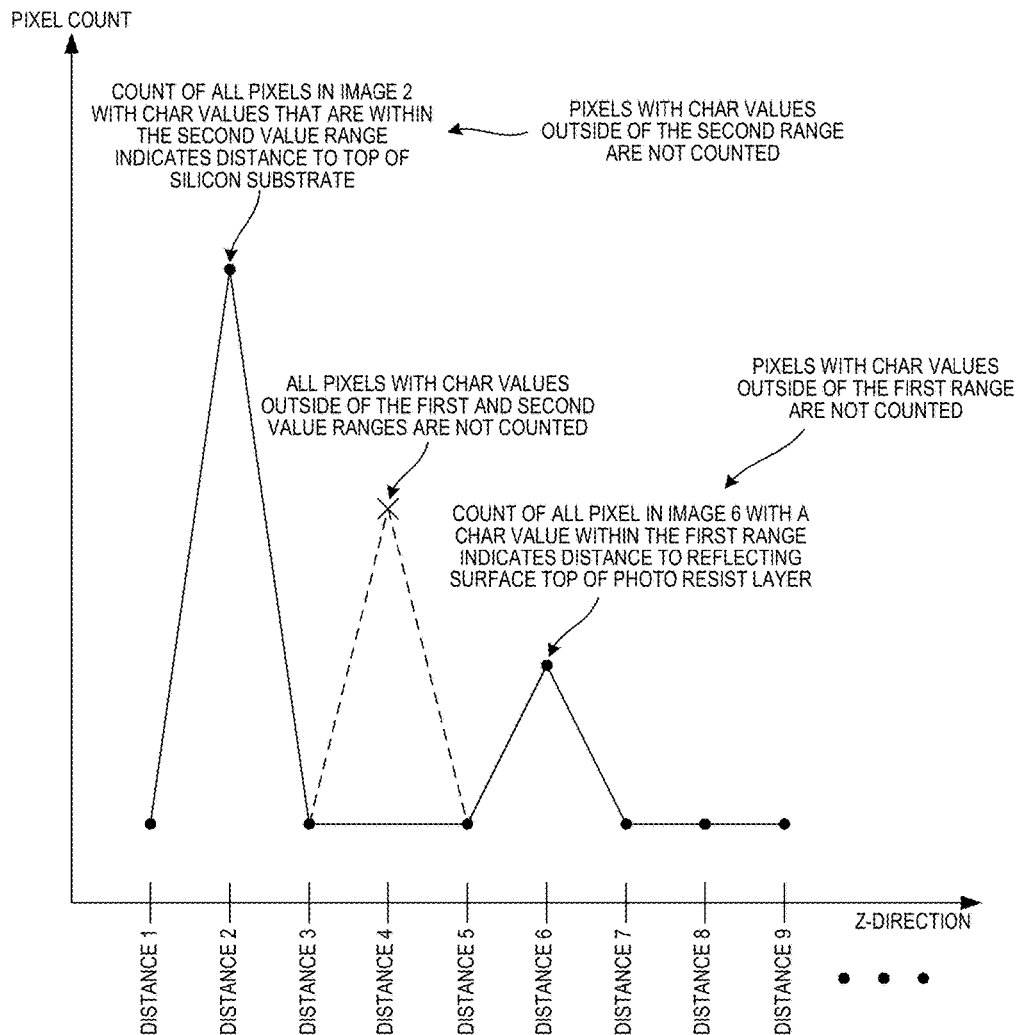
FIG. 14 is a chart illustrating the 3-D information resulting from the range mode operation.
Figure 15:
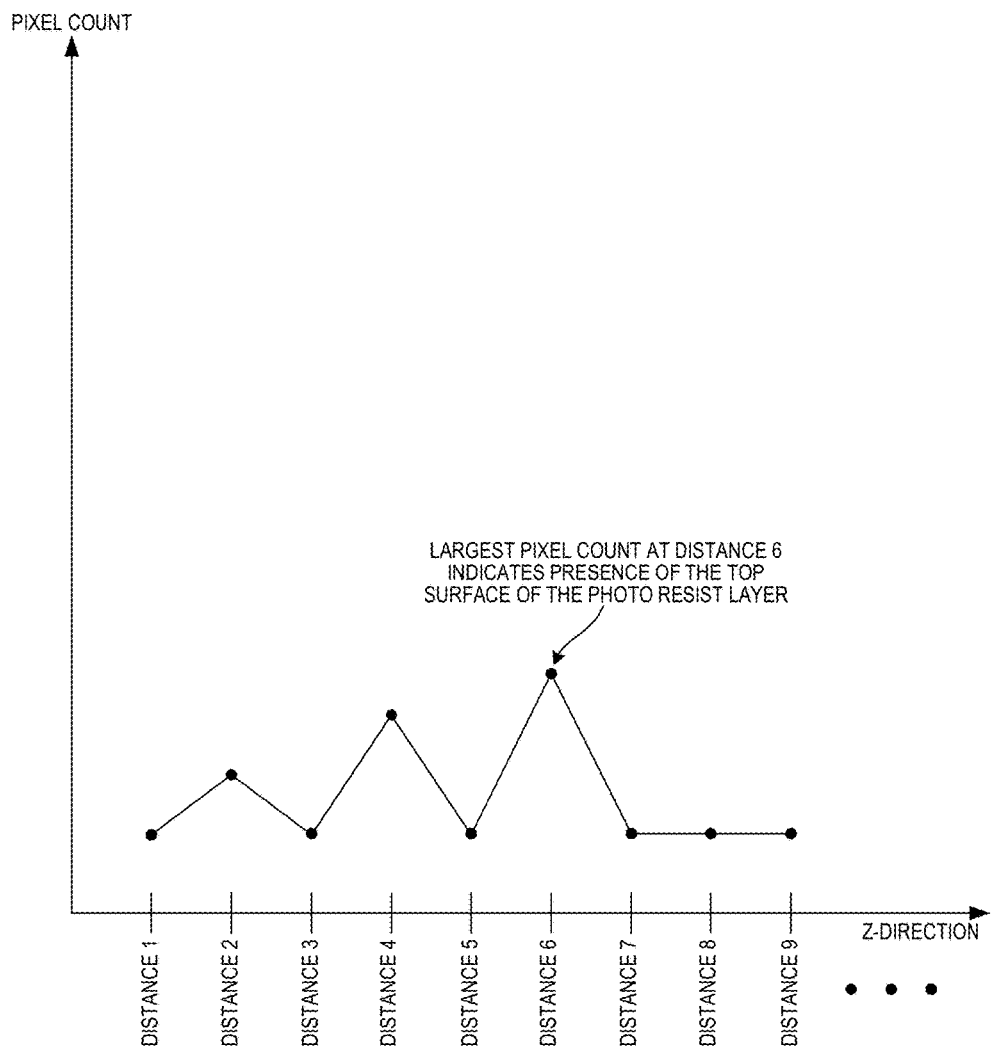
FIG. 15 is a chart illustrating only the count of pixels that have a characteristic value within a first range.

FIG. 14 is a chart illustrating the 3-D information resulting from the range mode operation. Given knowledge of the different types of material that are present on the wafer and the optical microscope configuration, an expected range of characteristic values can be determined for each material type. For example, photoresist layer will reflect a relative small amount of light that irradiates the top surface of the photoresist layer (i.e. 4%). Silicon layer will reflect light that irradiates the top surface of the silicon layer (i.e. 37%). The redirected reflections observed at distance 4 (i.e. 21%) will be substantially greater than the reflections observed at distance 6 from the top surface of the photoresist layer; however, the redirected reflections observed at distance 4 (i.e. 21%) will be substantially less than the reflection observed at distance 2 from the top surface of the silicon substrate. Therefore, when looking for the top surface of the photoresist layer, a first range that is centered on the expected characteristic value for photoresist can be used to filter out pixels that have characteristic values outside of the first range, thereby filtering out pixels that have characteristic values not resulting from reflections from the top surface of the photoresist layer. The pixel count across all distances generated by applying the first range of characteristic values is illustrated in FIG. 15. As shown in FIG. 15, some but not necessarily all pixels from other distances (surfaces) are filtered out by applying the first range. This occurs when the characteristic values measured at multiple distances fall within the first range. Nevertheless, application of the first range before counting pixels still functions to make the pixel count at the desired surface more prominent in comparison to other pixel counts at other distances. This is illustrated in FIG. 15. The pixel count at distance 6 is greater than the pixel count at distances 2 and 4 after the first range is applied, whereas before the first range was applied the pixel count at distance 6 was less than the pixel count at distances 2 and 4 (as shown in FIG. 14).

Figure 16:
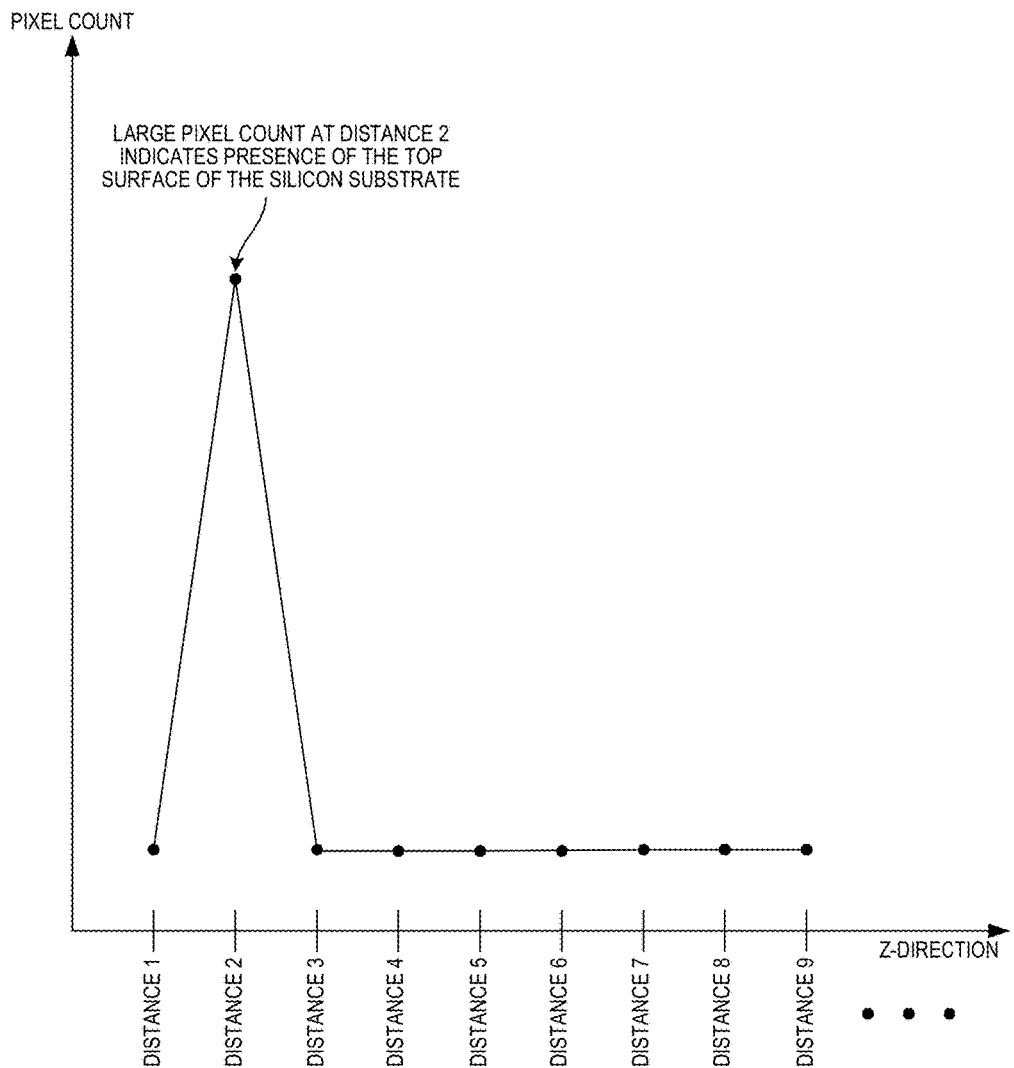
FIG. 16 is a chart illustrating only the count of pixels that have a characteristic value within a second range.

In a similar fashion, when looking for the top surface of the silicon substrate layer, a second range that is centered on the expected characteristic value for silicon substrate layer can be used to filter out pixels that have characteristic values outside of the second range, thereby filtering out pixels that have characteristic values not resulting from reflections from the top surface of the silicon substrate layer. The pixel count across all distances generated by applying the second range of characteristic values is illustrated in FIG. 16. This application of ranges reduces the false indication of a wafer surface located at distance 4 by virtue of the knowledge of what characteristic values are expected from all the material present on the wafer being scanned. As discussed regarding in FIG. 15, some but not necessarily all pixels from other distances (surfaces) are filtered out by applying a range. However, when the characteristic values measured at multiple distances do not fall within the same range, then the result of applying the range will eliminate all pixel counts from other distances (surfaces). FIG. 16 illustrates this scenario. In FIG. 16, the second range is applied before generating the pixel count at each distance. The result of applying the second range is that only pixels at distance 2 are counted. This creates a very clear indication that surface of the silicon substrate is located at distance 2.

It is noted, that reduce the impact caused by potential noise such as environmental vibration, a standard smoothing operation such as Gaussian filtering can be applied to the total pixel count along the z-distances before carrying out any peak searching operations.

Figure 17:
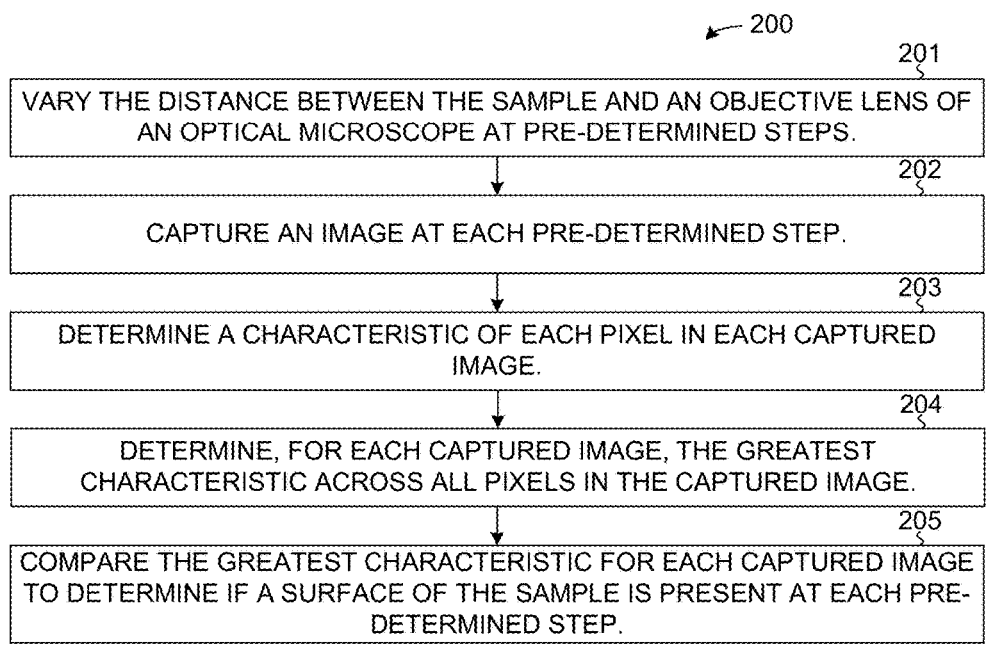
FIG. 17 is a flowchart illustrating the various steps included in peak mode operation.

FIG. 17 is a flowchart 200 illustrating the various steps included in peak mode operation. In step 201, the distance between the sample and the objective lens of an optical microscope is varied at pre-determined steps. In step 202, an image is captured at each pre-determined step. In step 203, a characteristic of each pixel in each captured image is determined. In step 204, for each captured image, the greatest characteristic across all pixels in the captured image is determined. In step 205, the greatest characteristic for each captured image is compared to determine if a surface of the sample is present at each pre-determined step.

Figure 18:
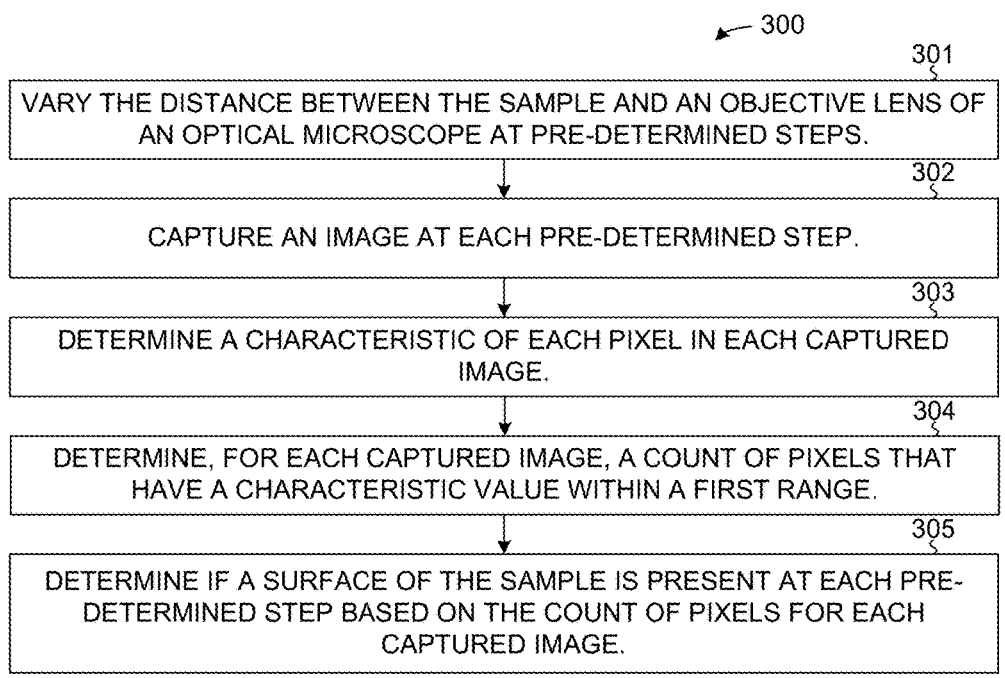
FIG. 18 is a flowchart illustrating the various steps included in range mode operation.

FIG. 18 is a flowchart 300 illustrating the various steps included in range mode operation. In step 301, the distance between the sample and the objective lens of an optical microscope is varied at pre-determined steps. In step 302, an image is captured at each pre-determined step. In step 303, a characteristic of each pixel in each captured image is determined. In step 304, for each captured image, a count of pixels that have a characteristic value within a first range is determined. In step 305, it is determined if a surface of the sample is present at each pre-determined step based on the count of pixels for each captured image.

Figure 19:
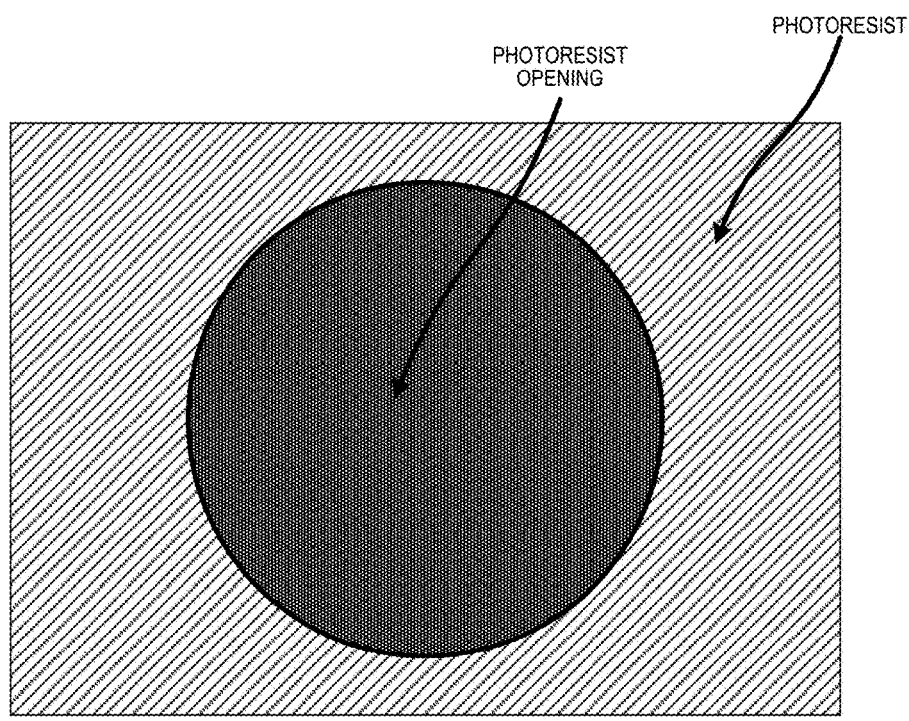
FIG. 19 is a diagram of a captured image, including a single feature, focused on the top surface of a photoresist layer.

FIG. 19 is a diagram of a captured image including a single feature. One example of a feature is an opening in the photoresist layer in the shape of a circle. Another example of a feature is an opening in the photoresist layer in the shape of trench, such as an unplated redistribution line (RDL) structure. During the wafer fabrication process the ability to measure various features of a photoresist opening in a wafer layer is advantageous. Measurement of a photoresist opening provides detection of flaws in the structure before metals are plated into the hole. For example, if a photoresist opening does not have the correct size, the plated RDL width will be wrong. Detection of this type of defect can prevent the further fabrication of a defective wafer. Preventing further fabrication of a defective wafer saves material and processing expenses. FIG. 19 illustrates that the measured intensity of light reflected from the top surface of the photoresist layer is greater than the measured intensity of light reflected from the opening in the photoresist layer when the captured image is focused on the top surface of the photoresist layer. As discussed in greater detail below, the information associated with each pixel in the captured image can be used to generate an intensity value for each pixel in the captured image. The intensity value of each pixel can then be compared with an intensity threshold to determine if each pixel is associated with a first region of the captured image, such as the top surface of the photoresist layer, or is associated with a second region of the captured image, such as the photoresist opening area. This can be done by (i) first applying an intensity threshold to the measured intensity of each pixel in the captured image, (ii) categorizing all pixels with an intensity value below the intensity threshold as being associated with a first region of the captured image, (iii) categorizing all pixels with an intensity value above the intensity threshold as being associated with a second region of the captured image, and (iv) defining a feature to be a group of pixels within the same region that are contiguous with other pixels associated with the same region.

The captured image shown in FIG. 19 may be a color image. Each pixel of the color image includes red, blue and green (RBG) channel values. Each of these color values can be combined to generate a single intensity value for each pixel. The various methods for converting the RBG values for each pixel to single intensity value are described below.

A first method is to use three weighted values to convert three color channels to an intensity value. Said another way, each color channel has its own weighted value or conversion factor. One can either use a default set of three conversion factors defined in a system recipe or modify them based on his sample measurement needs. A second method is to subtract the color channels for each pixel from a default color channel value for each color channel, the result of which is then converted into intensity values using the conversion factors discussed in the first method. A third method is to use a "color difference" scheme to convert the colors to intensity values. In a color difference scheme, the resultant pixel intensity is defined by how close a pixel's color is compared to a predefined fixed Red, Green and Blue color value. One example of color difference is the weighted vector distance between a pixel's color value and the fixed color value. Yet another method of "color difference", which is a color difference method with a fixed color value automatically derived from the image. In one example, where the border area of an image is known to be of the background color. The weighted average of the border area pixels' color can be used as the fixed color value for the color difference scheme.

Once the color image has been converted to an intensity image, an intensity threshold can be compared to the intensity of each pixel to determine the region of the image to which the pixel belongs. Said another way, a pixel with an intensity value above the intensity threshold indicates that the pixel received light reflected from a first surface of the sample, and a pixel with an intensity value below the intensity threshold indicates that the pixel did not receive light reflected from the first surface of the sample. Once each pixel in the image is mapped to a region, the approximate shape of the feature that is in focus in the image can be determined.

Figure 20:
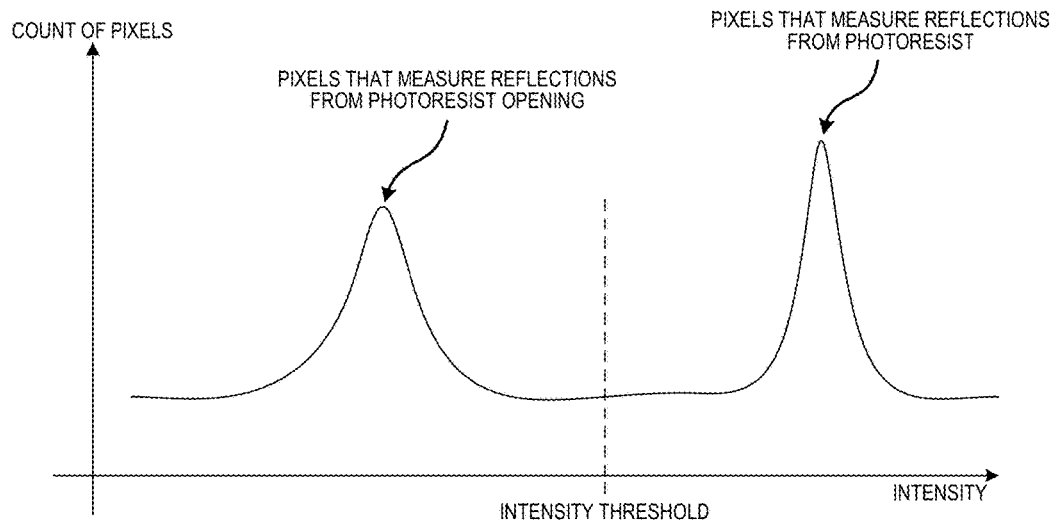
FIG. 20 is a diagram illustrating a first method of generating an intensity threshold.
Figure 21:
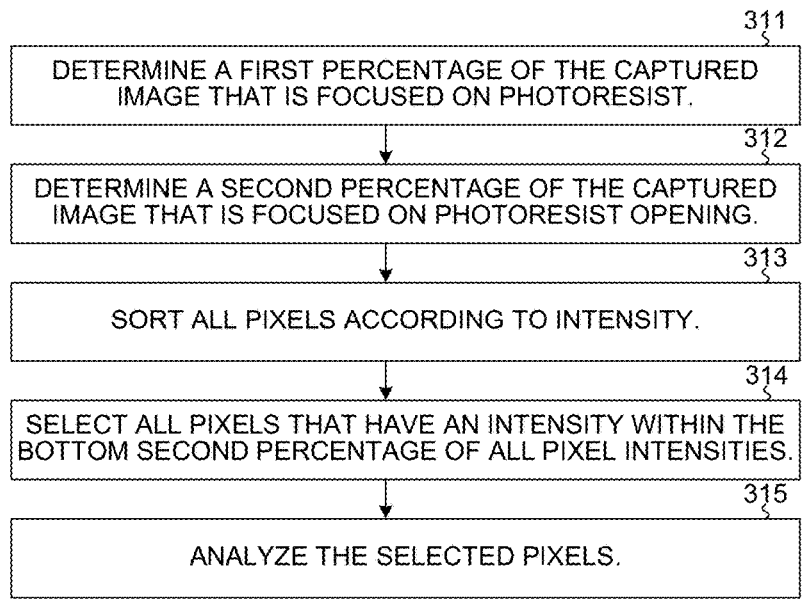
FIG. 21 is a diagram illustrating a second method of generate an intensity threshold.
Figure 22:
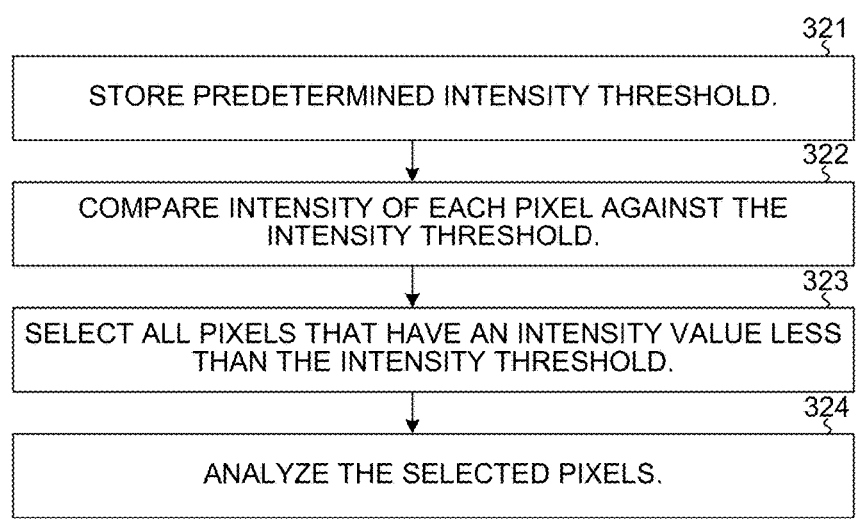
FIG. 22 is a diagram illustrating a third method of generate an intensity threshold.

FIG. 20, FIG. 21 and FIG. 22 illustrate three different methods of generating an intensity threshold value that can be used to differentiate pixels that measure light reflecting from the top surface of the photoresist layer from pixels that measure light not reflecting from the top surface of the photoresist layer.

FIG. 20 illustrates a first method of generating an intensity threshold value used for analyzing the captured image. In this first method, a count of pixels is generated for each measured intensity value. This type of graph is also referred to as a histogram. Once the count of pixels per intensity value is generated, the intensity range between the peak count of pixels resulting from measured light reflecting from the photoresist layer and the peak count of pixels resulting from measured light not reflecting from the photoresist layer can be determined. An intensity value within that range of intensity is selected to be the intensity threshold. In one example, the midpoint between the two peak counts is selected to be the threshold intensity. Other intensity values between the two peak counts may be used in other examples that fall within the disclosure of the present invention.

FIG. 21 is a second method of generating an intensity threshold value used for analyzing the captured image. In step 311, a determination is made as to a first percentage of the captured image that represents the photoresist region. This determination can be made by physical measurement, optical inspection or based on production specification. In step 312, a determination is made as to a second percentage of the captured image that represents the photoresist opening area. This determination can be made by physical measurement, optical inspection or based on production specification. In step 313, all pixels in the captured image are sorted according to the intensity measured by each pixel. In step 314, all pixels that have an intensity within the bottom second percentage of all pixel intensities are selected. In step 315, all selected pixels are analyzed.

FIG. 22 illustrates a third method of determining an intensity threshold value. In step 321, a predetermined intensity threshold is stored into memory. In step 322, the intensity of each pixel is compared against the stored intensity threshold. In step 323, all pixels that have an intensity value less than the intensity threshold are selected. In step 324, the selected pixels are analyzed.

Regardless of how the intensity threshold is generated, the threshold intensity value is used to determine roughly where the border of the feature in the captured image is located. The rough border of the feature will then be used to determine a much more accurate measurement of the border of the feature, as discussed below.

Figure 23:
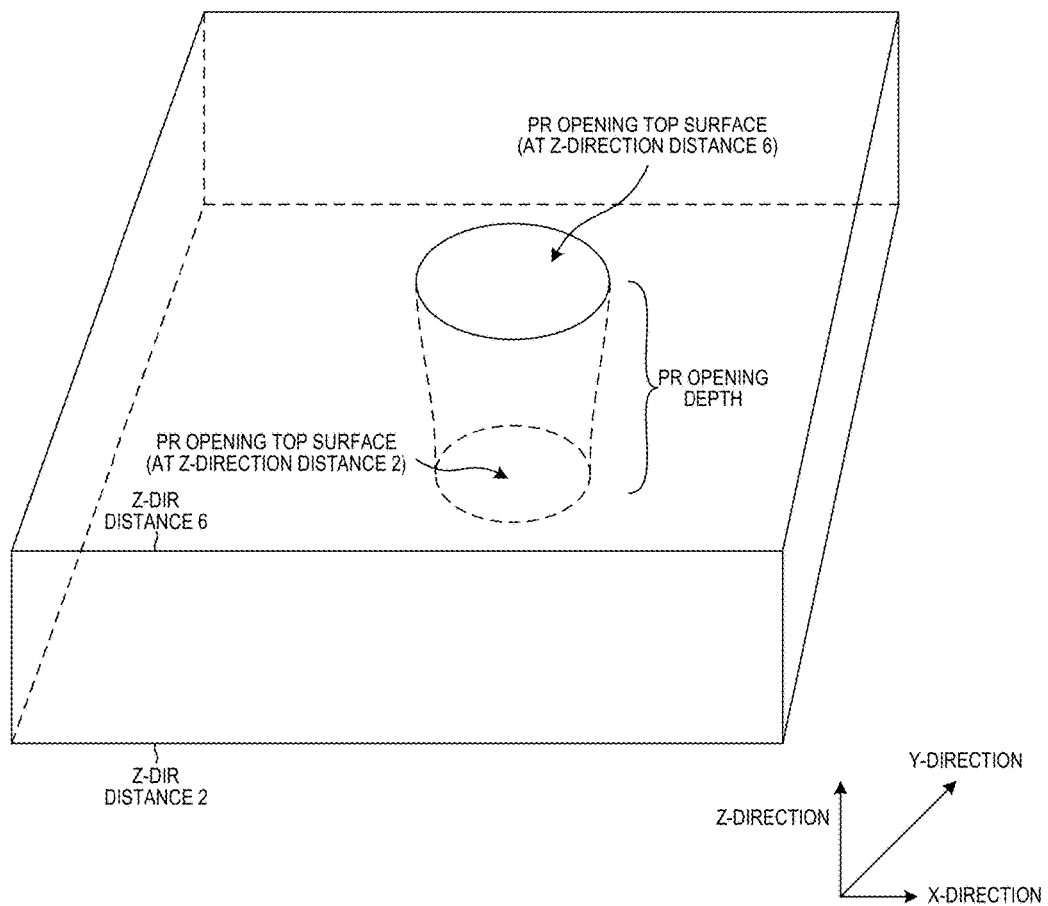
FIG. 23 is a 3-D diagram of a photoresist opening in a sample.

FIG. 23 is a 3-D diagram of a photoresist opening shown in FIG. 19. Various photoresist opening measurements are of interest during the fabrication process, such as the area of the top and bottom opening, the diameter of the top and bottom opening, the circumference of the top and bottom opening, the cross-sectional width of the top and bottom opening, and the depth of the opening. A first measurement is the top surface opening area. FIG. 8 (and the accompanying text) describes how an image focused on the top surface of the photoresist opening, and an image focused on the bottom surface of the photoresist opening, are selected from a plurality of images taken at different distances from the sample. Once the image focused on the top surface is selected, the image focused on the top surface of the photoresist opening may be used to determine the above mentioned top opening measurements. Likewise, once the image focused on the bottom surface of the photoresist opening is selected, the image focused on the bottom surface of the photoresist opening may be used to determine the above mentioned bottom opening measurements. As discussed above and in U.S. patent application Ser. No. 12/699,824, entitled "3-D Optical Microscope", filed Feb. 3, 2010, by James Jianguo Xu et al. (the subject matter of which is incorporated herein by reference), a pattern or grid may be projected onto the surface of the sample while multiple images are captured. In one example, an image including the projected pattern or grid is used to determine the photoresist opening measurements. In another example, a new image not including the pattern or grid, captured at the same z-distance is used to determine the photoresist opening measurements. In the latter example, the new image without a projected pattern or grid on the sample provides a "cleaner" image which provides easier detection of the border of the photoresist opening.

Figure 24:
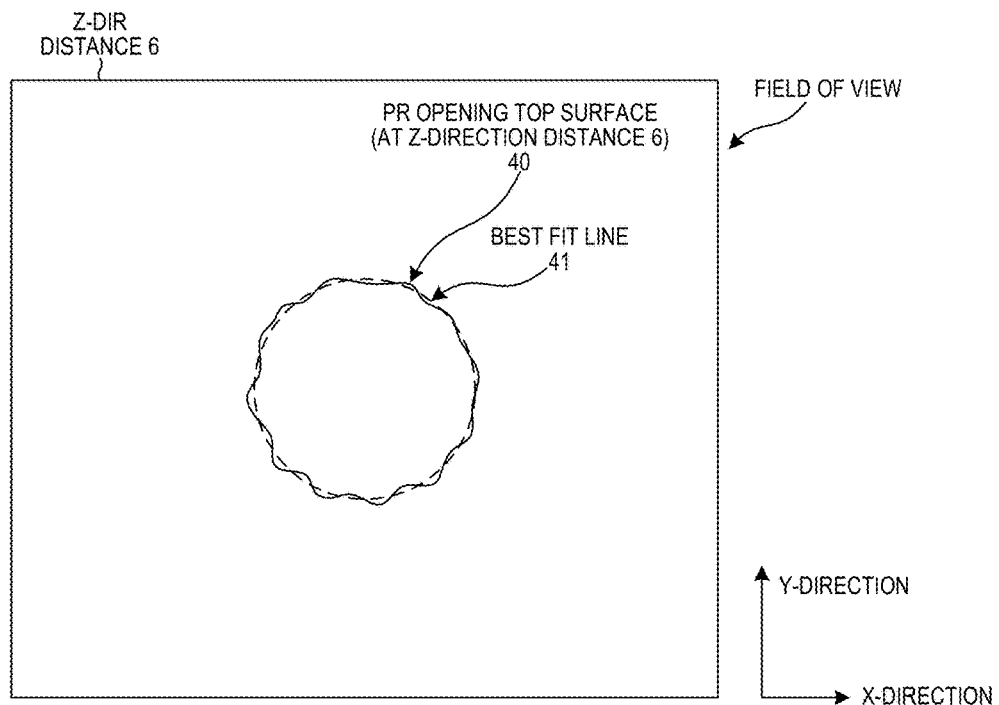
FIG. 24 is a 2-D diagram of the top surface opening of the photoresist shown in FIG. 23.

FIG. 24 is a 2-D diagram of the top surface opening shown in FIG. 23. The 2-D diagram clearly shows the border of the top surface opening (solid line) 40. The border is traced using a best fit line (the dashed line 41). Once the best fit line trace is created, the diameter, area and circumference of the best fit line 41 can be generated.

Figure 25:
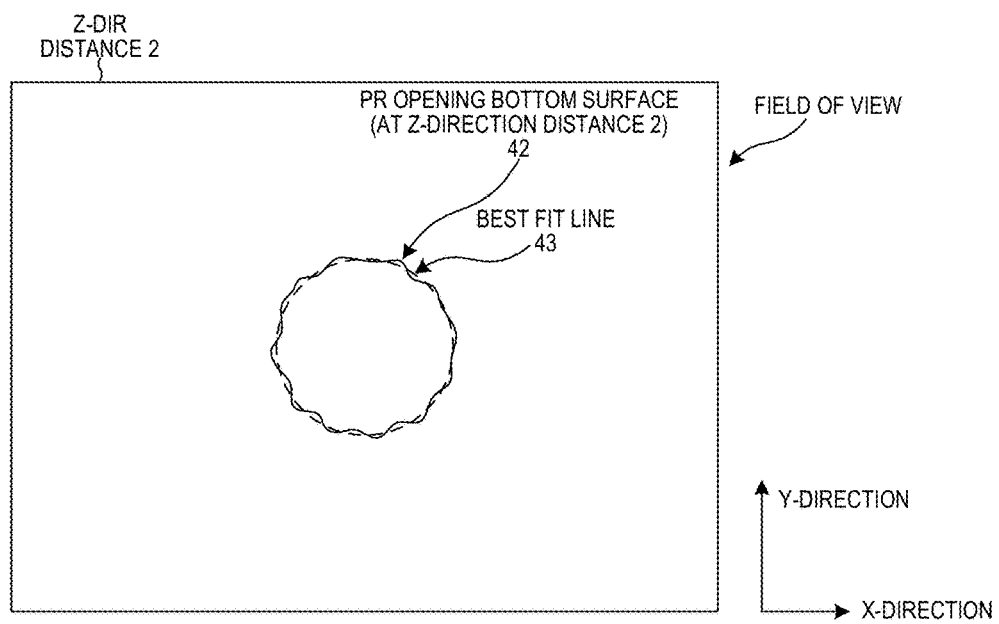
FIG. 25 is 2-D diagram of the bottom surface opening of the photoresist shown in FIG. 23.

FIG. 25 is 2-D diagram of the bottom surface opening shown in FIG. 23. The 2-D diagram clearly shows the border of the bottom surface opening (solid line 42). The border is traced using a best fit line (dashed line 43). Once the best fit line trace is created, the bottom surface opening diameter, area and circumference of the best fit line can be calculated.

In the present example, the best fit line is automatically generated by a computer system in communication with the optical microscope. The best fit line can be generated by analyzing transitions between dark and bright portions of the selected image, as is discussed in greater detail below.

Figure 26:
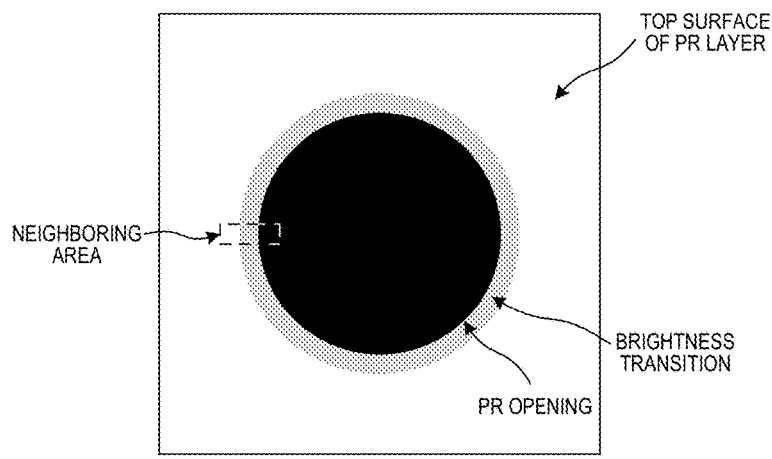
FIG. 26 is a captured image focused on a top surface of a photoresist layer.

FIG. 26 is a 2-D image of an opening in a photoresist layer. The image is focused on the top surface of the photoresist layer. In this example, the light reflecting from the top surface of the photoresist layer is bright because the microscope is focused on the top surface of the photoresist layer. The light intensity measured from the photoresist opening is dark because there is no reflecting surface in the photoresist opening. The intensity of each pixel is used to determine whether the pixel belongs to the top surface of the photoresist or the opening in the photoresist. The change in intensity from the transition between the top surface of the photoresist to the opening in the photoresist may span multiple pixels and multiple intensity levels. The image background intensity may also not be uniform. Therefore, further analysis is needed to determine exact pixel locations of the border of the photoresist. To determine the pixel location of a single surface transition point, an intensity average is taken within a neighboring bright area outside of the transition area, and an intensity average is taken within the neighboring dark area outside the transition area. The middle intensity value between the average of the neighboring bright area and the average of the neighboring dark area is used as the intensity threshold value that distinguishes whether a pixel belongs to the top surface of the photoresist or the opening in the photoresist. This intensity threshold may be different from the earlier discussed intensity threshold used to select the feature within a single captured image. Once the middle intensity threshold is determined, the middle intensity threshold is compared to all pixels to differentiate pixels that belong to the top surface of the photoresist or the opening in the photoresist. If the pixel intensity is above the intensity threshold, then the pixel is determined to be a photoresist pixel. If the pixel intensity is below the intensity threshold, then the pixel is determined to an opening area pixel. Multiple border points can be determined in this fashion and used to fit a shape. The fitted shape is then used to calculate the all desired dimensions of the top opening of the photoresist. In one example, the fitted shape may be selected from the group of: a circle, a square, a rectangle, a triangle, a oval, a hexagon, a pentagon, etc.

Figure 27:
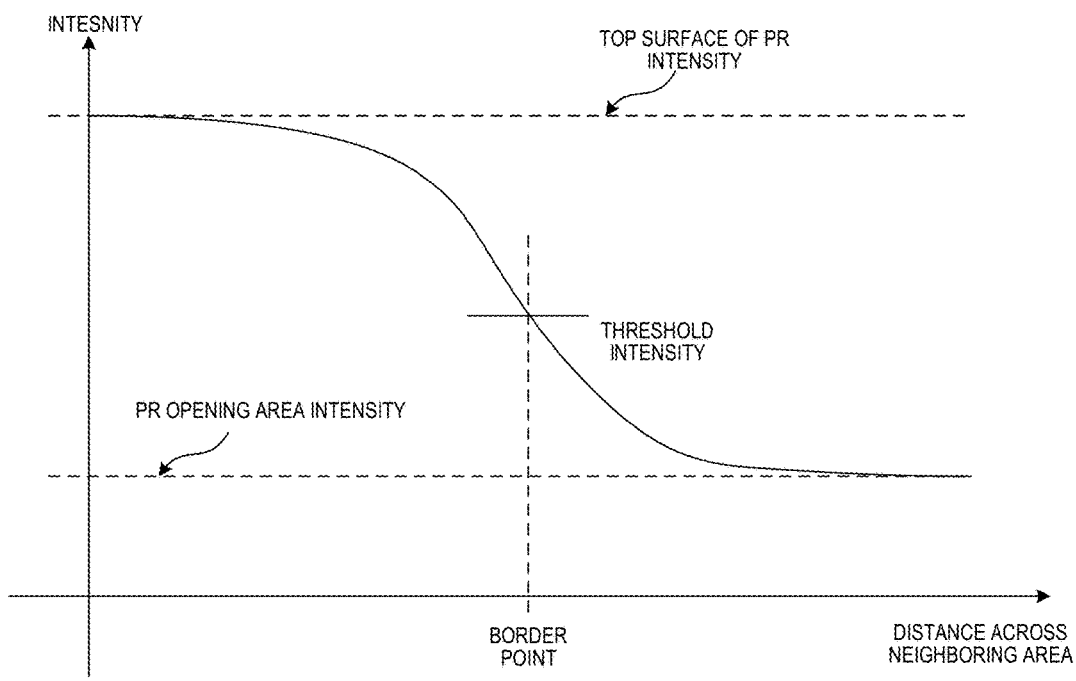
FIG. 27 is a diagram illustrating the detection of a border of the photoresist layer illustrated in FIG. 26.

FIG. 27 illustrates the variation of measured intensity across the neighboring area around the brightness transition of FIG. 26. At the left most portion of the neighboring area the measured intensity is high because the microscope is focused on the top surface of the photoresist layer. The measured light intensity decreases through the brightness transition of the neighboring area. The measured light intensity falls to a minimum range at the right most portion of the neighboring area because the top surface of the photoresist layer is not present in the right most portion of the neighboring area. FIG. 27 graphs this variation of measured intensity across the neighboring area. The border point indicating where the top surface of the photoresist layer ends can then be determined by application of a threshold intensity. The boarder point where the top surface of the photoresist ends is located at the intersection of the measured intensity and the threshold intensity. This process is repeated at different neighboring areas located along the brightness transition. For each neighboring area, a border point is determined. The border point for each neighboring area is then used to determine the size and shape of the top surface border.

Figure 28:
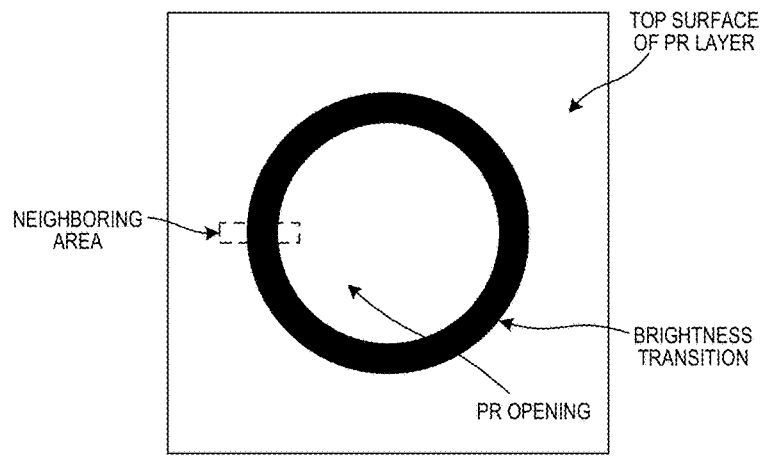
FIG. 28 is a captured image focused on a bottom surface of a photoresist layer.

FIG. 28 is a 2-D image of an opening in a photoresist layer. The image is focused on the bottom surface of photoresist opening. In this example, the light reflecting from the bottom surface of the photoresist opening area is bright because the microscope is focused on the bottom surface of the photoresist opening. The light reflecting from the photoresist area is also relatively bright because the substrate is either silicon or metal seed layer which has high reflectivity. The light reflecting from the border of the photoresist layer is dark due to light scattering caused by the photoresist border. The measured intensity of each pixel is used to determine if the pixel belongs to the bottom surface of the photoresist opening or not. The change in intensity from the transition between the bottom surface of the photoresist to the photoresist opening area may span multiple pixels and multiple intensity levels. The image background intensity may also not be uniform. Therefore, further analysis is needed to determine the exact pixel locations of the photoresist opening. To determine the pixel location of a border point, the location of a pixel with minimum intensity is determined within neighboring pixels. Multiple border points can be determined in this fashion, and are used to fit a shape. The fitted shape is then used to calculate the desired dimensions of the bottom opening.

Figure 29:
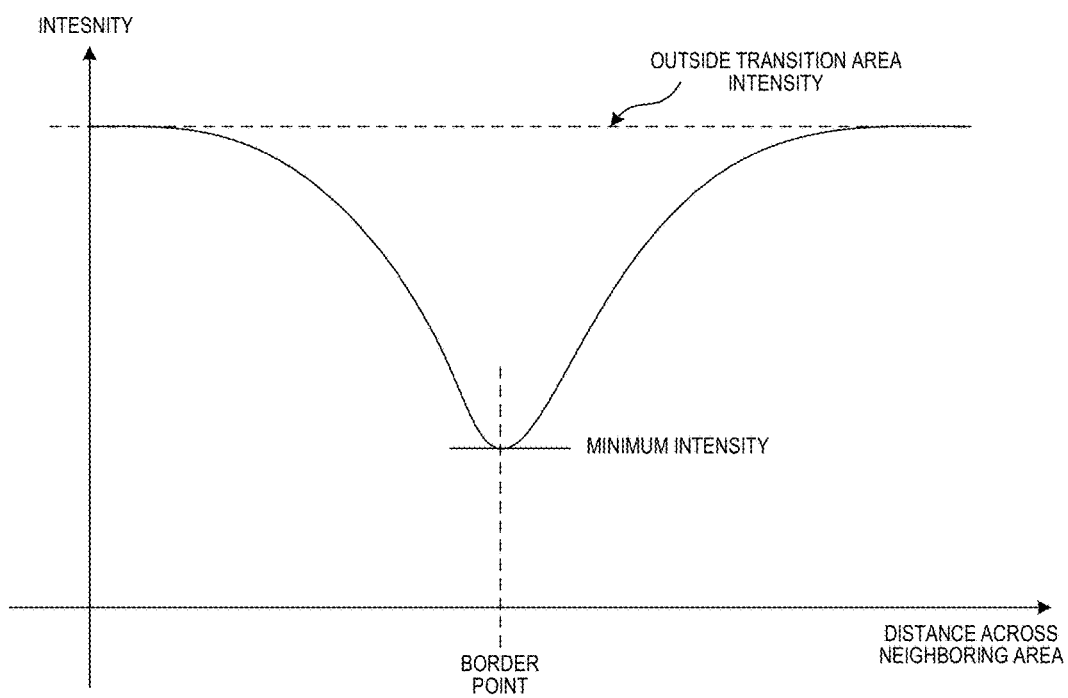
FIG. 29 is a diagram illustrating the detection of a border of the photoresist layer illustrated in FIG. 28.

FIG. 29 illustrates the variation of measured intensity across the neighboring area around the brightness transition of FIG. 28. At the left most portion of the neighboring area the measured intensity is high because the microscope is focused on the bottom surface of the photoresist opening. The measured light intensity decreases to a minimum intensity and then increases through the brightness transition of the neighboring area. The measured light intensity rises to a relatively high intensity range at the right most portion of the neighboring area due to light reflections from substrate surface. FIG. 29 graphs this variation of measured intensity across the neighboring area. The border point indicating where border of the photoresist opening is located can then be determined by finding the location of the minimum measured intensity. The boarder point is located where the minimum measured intensity is located. The process is repeated at different neighboring areas located along the brightness transition. For each neighboring area, a border point is determined. The border point for each neighboring area is then used to determine the size and shape of the bottom surface border.

Figure 30:
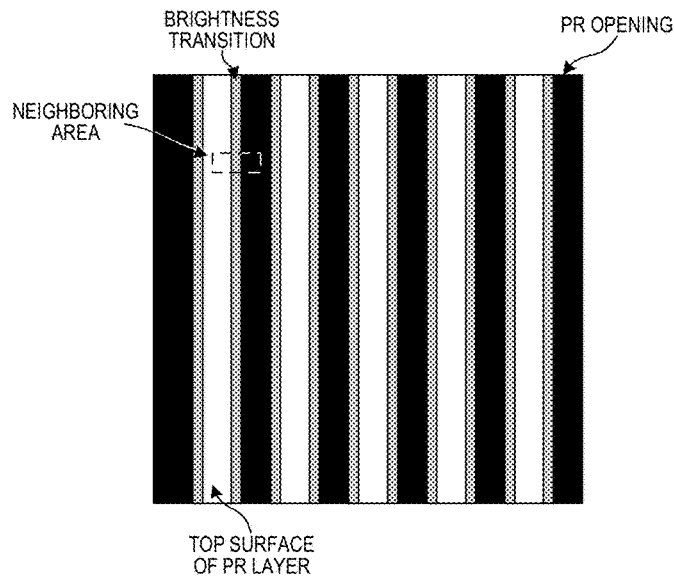
FIG. 30 is a captured image focused on a top surface of a photoresist layer in a trench structure.

FIG. 30 is a 2-D image of a trench structure in a photoresist layer, such as an unplated redistribution line (RDL) structure. The image is focused on the top surface of the photoresist layer. In this example, the light reflecting from the top surface of the photoresist layer is bright because the microscope is focused on the top surface of the photoresist layer. The light reflecting from the opening in the photoresist layer is darker because less light is reflected from the open trench area. The intensity of each pixel is used to determine whether the pixel belongs to the top surface of the photoresist or the opening area in the photoresist. The change in intensity from the transition between the top surface of the photoresist to the opening area in the photoresist may be span multiple pixels and multiple intensity levels. The image background intensity may also not be uniform. Therefore, further analysis is needed to determine exact pixel locations of the border of the photoresist. To determine the pixel location of a single surface transition point, an intensity average is taken within a neighboring bright area outside of the transition area, and an intensity average is taken within the neighboring dark area outside the transition area. The middle intensity value between the average of the neighboring bright area and the average of the neighboring dark area is used as the intensity threshold value to distinguish top surface photoresist reflections from non-top surface photoresist reflections. Once the middle intensity threshold is determined, the middle intensity threshold is compared to all neighboring pixels to determine a border between the top surface pixels and the photoresist opening area. If the pixel intensity is above the intensity threshold, then the pixel is determined to be a top surface photoresist pixel. If the pixel intensity is below the intensity threshold, then the pixel is determined to be a photoresist opening area pixel. Multiple border points can be determined in this fashion and used to fit a shape. The fitted shape is then used to calculate the all desired dimensions of the photoresist opening of the trench such as trench width.

Figure 31:
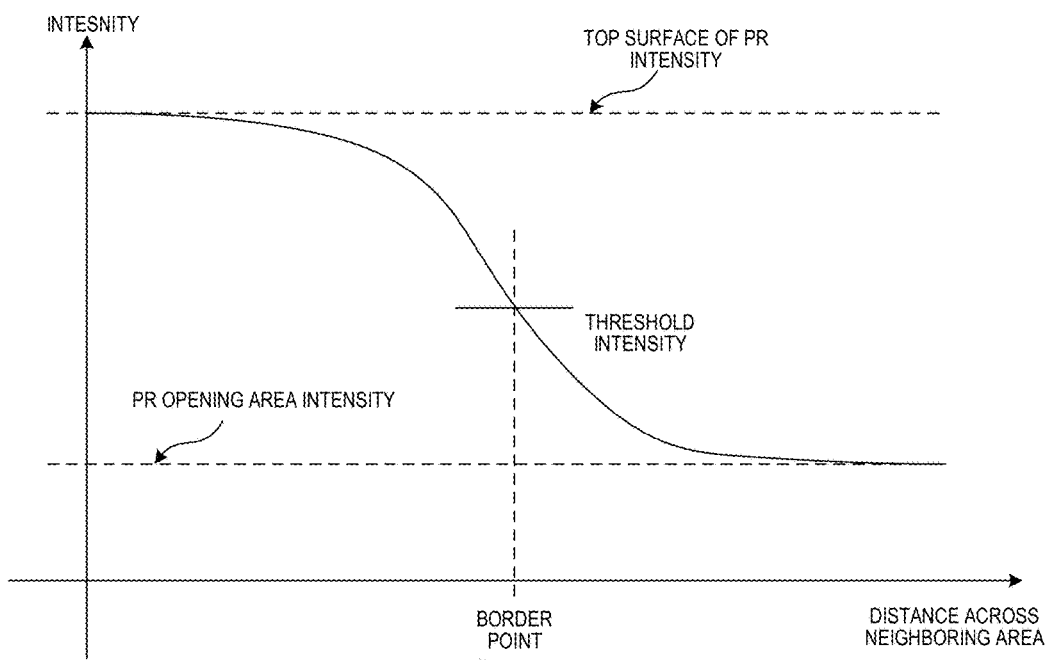
FIG. 31 is a diagram illustrating the detection of a border of the photoresist layer illustrated in FIG. 30.

FIG. 31 illustrates the variation of measured intensity across the neighboring area around the brightness transition of FIG. 30. At the left most portion of the neighboring area the measured intensity is high because the microscope is focused on the top surface of the photoresist layer. The measured light intensity decreases through the brightness transition of the neighboring area. The measured light intensity falls to a minimum range at the right most portion of the neighboring area because the top surface of the photoresist layer is not present in the right most portion of the neighboring area. FIG. 31 graphs this variation of measured intensity across the neighboring area. The border point indicating where the top surface of the photoresist layer ends can then be determined by application of a threshold intensity. The boarder point where the top surface of the photoresist ends is located at the intersection of the measured intensity and the threshold intensity. This process is repeated at different neighboring areas located along the brightness transition. For each neighboring area, a border point is determined. The border point for each neighboring area is then used to determine the size and shape of the top surface border.

With respect of FIG. 26 through FIG. 31, pixel intensity is only one example of pixel characteristics that can be used to distinguish pixels of different regions in an image. For example, the wavelengths, or colors, of each pixel may also be used to distinguish pixels from different regions in an image in a similar fashion. Once the border between each region is accurately defined, it is then used to determine the critical dimensions (CD) of a PR opening such as its diameter or width. Often times, the measured CD values are then compared with those measured on other types of tools such as a critical dimension-scanning electron microscope (CD-SEM). This kind of cross-calibration is necessary to ensure measurement precision among production monitoring tools.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method of generating three-dimensional (3-D) information of a sample using an optical microscope, the method comprising:
    varying the distance between the sample and an objective lens of the optical microscope at pre-determined steps;
    capturing an image at each pre-determined step, wherein a first surface of the sample and a second surface of the sample are within a field of view of each of the captured images;
    determining a characteristic value of each pixel in each captured image;
    determining a first captured image that is focused on a first surface of the sample based on the characteristic value of each pixel in each captured image;
    determining a measurement of an opening in the first surface of the sample based on the first captured image;
    determining a second captured image that is focused on a second surface of the sample based on the characteristics of each pixel in each captured image;
    determining a measurement of an opening in the second surface of the sample based on the second captured image; and
    determining a distance between the first surface of the sample and the second surface of the sample, wherein the distance between the first surface of the sample and the second surface of the sample indicates the depth of the opening in the sample.

2. The method of claim 1, wherein the opening in the first surface of the sample is an opening area of a bottom of a hole or trench in the sample.

3. The method of claim 1, wherein the opening in the first surface of the sample is an opening area of a top of a hole or trench in the sample.

4. The method of claim 1, wherein the determining of the measurement includes fitting a line to a boundary of the opening in the first surface of the sample shown in the first captured image.

5. The method of claim 1, wherein the measurement is a diameter of the opening in the first surface of the sample.

6. The method of claim 1, wherein the measurement is an area of the opening in the first surface of the sample.

7. The method of claim 1, wherein the measurement is a width of the opening in the first surface of the sample.

8. The method of claim 1, wherein the measurement is a shape of the opening in the first surface of the sample.

9. The method of claim 1, wherein the characteristic of each pixel is intensity.

10. The method of claim 1, wherein the characteristic of each pixel is contrast.

11. The method of claim 1, wherein the characteristic of each pixel is fringe contrast.

12. The method of claim 1, wherein the optical microscope includes a stage, wherein the sample is supported by the stage, wherein the optical microscope is adapted to communicate with a computer system, and wherein the computer system includes a memory device that is adapted to store each captured image.

13. The method of claim 1, wherein the optical microscope is a confocal microscope.

14. The method of claim 1, wherein the optical microscope is a structured illumination microscope.

15. The method of claim 1, wherein the optical microscope is an interferometer microscope.

16. The method of claim 1, wherein the determining a first captured image that is focused on a first surface of the sample, further comprises:
    determining, for each captured image, the greatest characteristic across all pixels in the captured image; and
    comparing the greatest characteristic for each captured image to determine if a surface of the sample is present at each pre-determined step.

17. The method of claim 1, wherein the determining a first captured image that is focused on a first surface of the sample, further comprises:
    determining, for each captured image, a count of pixels that have a characteristic value within a first range, wherein all pixels that do not have a characteristic value within the first range are not included in the count of pixels; and
    determining if a surface of the sample is present at each pre-determined step based on the count of pixels for each captured image.

18. A three-dimensional (3-D) measurement system, comprising:
    a optical microscope comprising a objective lens and a stage, wherein the optical microscope is adapted to vary the distance between a sample supported by the stage and the objective lens of the optical microscope at pre-determined steps; and
    a computer system comprising a processor and a storage device, wherein the computer system is adapted to:
        store an image captured at each pre-determined step, wherein a first surface of the sample and a second surface of the sample is within a field of view of each image;
        determine a characteristic of each pixel in each captured image;
        determine a first captured image that is focused on the first surface of the sample based on the characteristics of each pixel in each captured image;
        determining a measurement of an opening in the first surface of the sample based on the first captured image;
    determining a second captured image that is focused on a second surface of the sample based on the characteristics of each pixel in each captured image;
    determining a measurement of an opening in the second surface of the sample based on the second captured image; and
    determining a distance between the first surface of the sample and the second surface of the sample, wherein the distance between the first surface of the sample and the second surface of the sample indicates the depth of the opening in the sample.

19. A method of generating three-dimensional (3-D) information of a sample using an optical microscope, the method comprising:

varying the distance between the sample and an objective lens of the optical microscope at pre-determined steps;

capturing an image at each pre-determined step, wherein a pattern is projected onto the sample while each image is captured, and wherein a first surface of the sample and a second surface of the sample is within a field of view of each of the captured images;

determining a characteristic value of each pixel in each captured image;

determining a first captured image that is focused on a first surface of the sample based on the characteristic value of each pixel in each captured image, wherein the first captured image is focused at a focal distance;

capturing a second image taken at the focal distance, wherein a pattern is not projected onto the sample while the second image is captured;

determining a measurement of an opening in the first surface of the sample based on the second captured image;

determining a second captured image that is focused on a second surface of the sample based on the characteristics of each pixel in each captured image;

determining a measurement of an opening in the second surface of the sample based on the second captured image; and determining a distance between the first surface of the sample and the second surface of the sample, wherein the distance between the first surface of the sample and the second surface of the sample indicates the depth of the opening in the sample.

* * * * *